(12) United States Patent
Ohya et al.

(10) Patent No.: US 9,512,149 B2
(45) Date of Patent: Dec. 6, 2016

(54) REACTIVE COMPOUND

(71) Applicant: SUMITOMO CHEMICAL COMPANY, LIMITED, Tokyo (JP)

(72) Inventors: Kenichiro Ohya, Tsukuba (JP); Ken Yoshimura, Tsukuba (JP)

(73) Assignee: SUMITOMO CHEMICAL COMPANY, LIMITED, Tokyo (JP)

( * ) Notice: Subject to any disclaimer, the term of this patent is extended or adjusted under 35 U.S.C. 154(b) by 0 days.

(21) Appl. No.: 14/761,337

(22) PCT Filed: Jan. 17, 2014

(86) PCT No.: PCT/JP2014/051430
§ 371 (c)(1),
(2) Date: Jul. 16, 2015

(87) PCT Pub. No.: WO2014/112656
PCT Pub. Date: Jul. 24, 2014

(65) Prior Publication Data
US 2015/0353583 A1 Dec. 10, 2015

(30) Foreign Application Priority Data

Jan. 21, 2013 (JP) .................................. 2013-008096
Nov. 19, 2013 (JP) .................................. 2013-238580

(51) Int. Cl.
| | | |
|---|---|---|
| C08G 75/00 | (2006.01) |
| C07F 5/04 | (2006.01) |
| C08G 75/32 | (2006.01) |
| C08G 61/12 | (2006.01) |
| H01L 51/00 | (2006.01) |
| H01L 51/42 | (2006.01) |

(52) U.S. Cl.
CPC ............... *C07F 5/04* (2013.01); *C08G 61/122* (2013.01); *C08G 61/123* (2013.01); *C08G 61/126* (2013.01); *C08G 75/32* (2013.01); *H01L 51/0036* (2013.01); *C08G 2261/124* (2013.01); *C08G 2261/146* (2013.01); *C08G 2261/1412* (2013.01); *C08G 2261/3223* (2013.01); *C08G 2261/3243* (2013.01); *C08G 2261/3246* (2013.01); *C08G 2261/344* (2013.01); *C08G 2261/411* (2013.01); *H01L 51/42* (2013.01)

(58) Field of Classification Search
CPC . C08K 3/04; H01L 51/0043; H01L 51/0036; H01L 51/4253; C08G 61/122; C08G 61/123; C08G 2261/146
See application file for complete search history.

(56) References Cited

FOREIGN PATENT DOCUMENTS

| | | |
|---|---|---|
| JP | 2009506519 A | 2/2009 |
| JP | 201199069 A | 5/2011 |
| WO | 2007011739 A2 | 1/2007 |
| WO | 2012133874 A1 | 10/2012 |

OTHER PUBLICATIONS

Laura M. Lanni, et al., "Self-assembling Boronate-linked Materials: Stability and Sensing", Department of Chemistry and Biochemistry, University of South Carolina, Columbia, SC 29208, 2012, pp. 251-252.

Yasunori Yamamoto, et al., "Cyclic Triolborates: Air- and Water-Stable Ate Complexes of Organoboronic Acids", Angew. Chem. Int. Ed. 2008, 47, pp. 928-931.

*Primary Examiner* — Shane Fang
(74) *Attorney, Agent, or Firm* — Sughrue Mion, PLLC

(57) ABSTRACT

A reactive compound represented by the following formula (I):

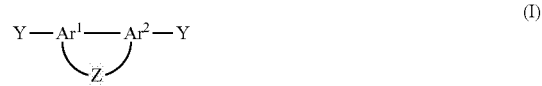

in the formula (I), Z represents a divalent group. A plurality of Y may be the same or different, and represent a monovalent boronate residue having at least one hydroxyl group, $Ar^1$ and $Ar^2$ may be the same or different, and represent a trivalent aromatic hydrocarbon group or a trivalent heterocyclic group.

8 Claims, No Drawings

REACTIVE COMPOUND

CROSS REFERENCE TO RELATED APPLICATIONS

This application is a National Stage of International Application No. PCT/JP2014/051430 filed Jan. 17, 2014, claiming priority based on Japanese Patent Application No. 2013-008096 filed Jan. 21, 2013 and Japanese Patent Application No 2013-238580 filed Nov. 19, 2013, the contents of all of which are incorporated herein by reference in their entirety.

TECHNICAL FIELD

The present invention relates to a reactive compound having a specific structure.

BACKGROUND ART

In late years, $CO_2$ released into the atmosphere is required to reduce for prevention of global warming. There is a suggestion on adoption of a solar system using a silicon based solar battery of pn junction type as one embodiment of electronic devices. However, monocrystal silicon, polycrystal silicon and amorphous silicon as materials of a silicon based solar battery need high temperature and high vacuum processes in production thereof.

In contrast, for an organic film solar battery containing an organic layer containing a polymer compound, high temperature and high vacuum processes used for production of a silicon based solar battery can be omitted, thus, the organic film solar battery can possibly be produced at low cost via only an application process, and is attracting attention recently. As a polymer compound used in an organic film solar battery, a polymer compound composed of a repeating unit (A) and a repeating unit (B) is known (Patent document 1).

repeating unit (A)

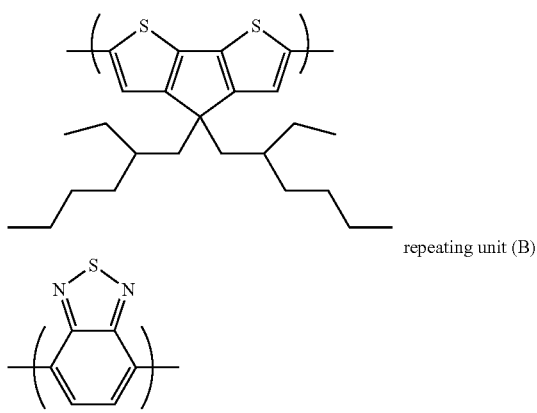

repeating unit (B)

PRIOR ART DOCUMENT

Patent Document

Patent document 1: Japanese Patent Application National Publication (Lai-open) No. 2009-506519

SUMMARY OF THE INVENTION

However, since most monomers used for synthesis of the abov-described polymer compound are in the form of oil, it is hard to improve its purity by r-crystallization and the like, and precise control of polymerization thereof is difficult.

The present invention has an object of providing a reactive compound capable of easily improving its purity.

The present invention is as described below.

[1] A reactive compound represented by the formula (I):

(I)

[In the formula (I), Z represents a divalent group. A plurality of Y may be the same or different, and represent a monovalent boronate residue having at least one hydroxyl group, $Ar^1$ and $Ar^2$ may be the same or different, and represent a trivalent aromatic hydrocarbon group or a trivalent heterocyclic group.].

[2] The reactive compound according to [1], wherein $Ar^1$ and $Ar^2$ are a trivalent heterocyclic group.

[3] The reactive compound according to [1] or [2], wherein Y is a group represented by the following formula (Y'-1), (Y'-2) or (Y'-3):

(Y'-1)

(Y'-2)

(Y'-3)

[In the formulae (Y'-1), (Y'-2) and (Y'-3), R' is a substituent represented by the following formula (R'-1), (R'-2) or (R'-3). R" represents a hydrogen atom, a methyl group or an ethyl group. n and m each represent an integer, and satisfy $n \geq 1$, $m \geq 0$ and $n+m \leq 4$.]

(R'-1)

(R'-2)

(R'-3)

[In the formulae (R'-1), (R'-2) and (R'-3), a plurality of R''' are the same or different from each other, and represent a hydrogen atom, a methyl group or an ethyl group.].

[4] The reactive compound according to any one of [1] to [3], wherein Z is a group represented by any one of the following formulae (Z-1) to (Z-7):

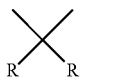 (Z-1)

 (Z-2)

 (Z-3)

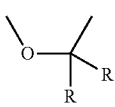 (Z-4)

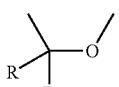 (Z-5)

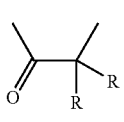 (Z-6)

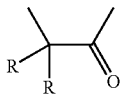 (Z-7)

[In the formulae (Z-1) to (Z-7), a plurality of R are the same or different from each other, and represent a hydrogen atom, a halogen atom or a substituent.].

[5] The reactive compound according to any one of [1] to [4], wherein the reactive compound represented by the formula (I) is a compound represented by the following formula (II):

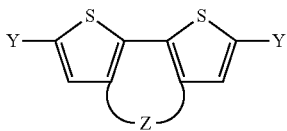 (II)

[In the formula (II), Z represents the same meaning as described above, Y represents the same meaning as described above.]

[6] The reactive compound according to any one of [1] to [5], wherein Y is a group represented by the following formula (Y-1), (Y-2) or (Y-3):

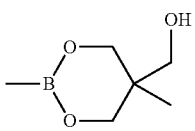 (Y-1)

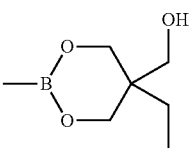 (Y-2)

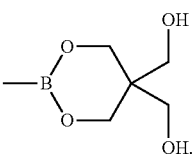 (Y-3)

[7] The reactive compound according to any one of [1] to [6], wherein the reactive compound represented by the formula (I) is a compound represented by the following formula (III-1) or (III-2):

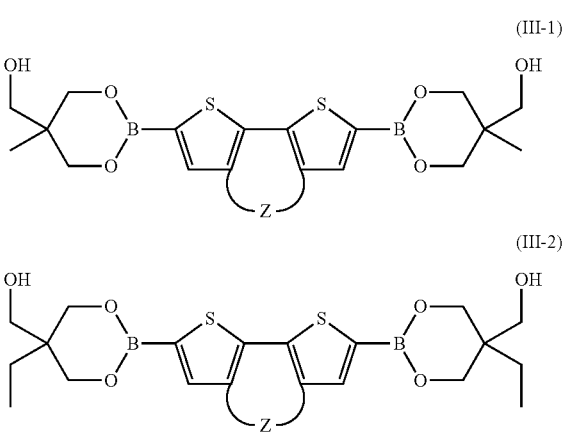 (III-1)

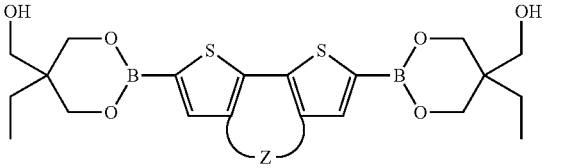 (III-2)

[In the formulae (III-1) and (III-2), Z represents the same meaning as described above.].

[8] The reactive compound according to any one of [1] to [7], wherein the reactive compound represented by the formula (I) is a compound represented by the following formula (IV-1) or (IV-2):

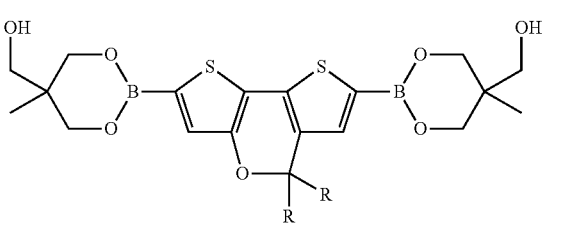 (IV-1)

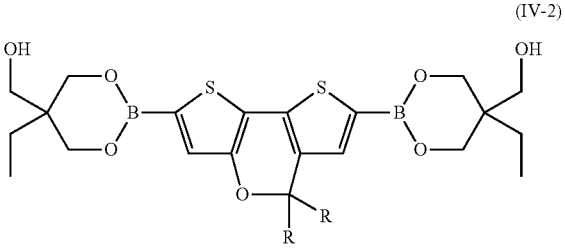 (IV-2)

[In the formulae (IV-1) and (IV-2), a plurality of R'''' are the same or different from each other, and represent a hydrogen atom or a substituent.].

[9] A method of producing a polymer compound containing a constituent unit represented by the following formula (VI) and a constituent unit represented by the following formula (VII),

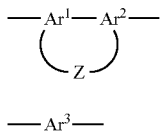
(VI)

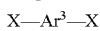
(VII)

comprising reacting the reactive compound according to any one of [1] to [8] with a compound represented by the following formula (V):

$$X—Ar^3—X \quad (V)$$

[In the formula (VI), $Ar^1$, $Ar^2$ and Z represent the same meaning as described above. In the formula (VII), $Ar^3$ represents a divalent aromatic hydrocarbon group or a divalent heterocyclic group. In the formula (V), $Ar^3$ represents the same meaning as described above, and a plurality of X are the same or different from each other, and represent a halogen atom.].

MODES FOR CARRYING OUT THE INVENTION

The present invention will be illustrated in detail below.

The reactive compound of the present invention is represented by the following formula (I).

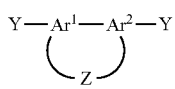
(I)

The reactive compound of the present invention may advantageously be a compound capable of reacting, for example, according to the Suzuki coupling reaction, and its use is not particularly restricted. The reactive compound of the present invention may be used without reacting, providing it is a compound represented by the formula (I).

In the formula (1), Z represents a divalent group, and Y represents a boronate residue having a hydroxyl group. Two Y may be the same or different, and it is preferable that they are the same from the standpoint of easiness of synthesis of the compound. $Ar^1$ and $Ar^2$ may be the same or different, and represent a trivalent aromatic hydrocarbon group or a trivalent heterocyclic group.

The divalent group represented by Z in the formula (I) includes, for example, divalent groups containing at least one atom selected from the group consisting of a carbon atom having a $sp^3$ hybridized orbital, a silicon atom having a $sp^3$ hybridized orbital, a nitrogen atom having a $sp^3$ hybridized orbital and an oxygen atom having a sp hybridized orbital in the main chain (namely, as an atom constituting the ring). As the divalent group represented by Z, groups represented by the following formulae (Z-1) to (Z-7) are preferable, and more preferable from the standpoint of an improvement in purity of the reactive compound is a group represented by the formula (Z-4) or the formula (Z-5).

(Z-1)

(Z-2)

(Z-3)

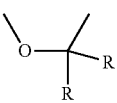
(Z-4)

(Z-5)

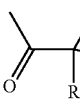
(Z-6)

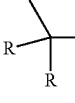
(Z-7)

[In the formulae (Z-1) to (Z-7), a plurality of R are the same or different from each other, and represent a hydrogen atom, a halogen atom or a substituent.]

In the formulae (Z-1) to (Z-7), R represents a hydrogen atom, a halogen atom or a substituent. The substituent is a monovalent group. Examples of the substituent include an optionally substituted alkyl group, an optionally substituted alkoxy group, an optionally substituted alkylthio group, an aryl group, an aryloxy group, an arylthio group, an optionally substituted arylalkyl group, an optionally substituted arylalkoxy group, an optionally substituted arylalkylthio group, an optionally substituted acyl group, an optionally substituted acyloxy group, an optionally substituted amide group, an optionally substituted acid imide group, an amino group, a substituted amino group, a substituted silyl group, a substituted silyloxy group, a substituted silylthio group, a substituted silylamino group, a monovalent heterocyclic group, a heterocyclic oxy group, a heterocyclic thio group, an arylalkenyl group, an arylalkynyl group, a carboxyl group and a cyano group. When there are a plurality of R in any of the formulae (Z-1) to (Z-7), they may be the same or different from each other.

The halogen atom represented by R includes a fluorine atom, a chlorine atom, a bromine atom and an iodine atom, preferably a fluorine atom.

The optionally substituted alkyl group may be linear or branched, and may also be a cycloalkyl group. The number of carbon atoms of the alkyl group is usually 1 to 30. The substituent which the alkyl group may have includes, for example, a halogen atom. Specific examples of the halogen atom are the same as specific examples of the halogen atom represented by R. Specific examples of the optionally substituted alkyl group include linear alkyl groups such as a methyl group, an ethyl group, a propyl group, an isopropyl group, a butyl group, an isobutyl group, a sec-butyl group, a ter-butyl group, a pentyl group, an isopentyl group, a 2-methylbutyl group, a 1-methylbutyl group, a hexyl group, an isohexyl group, a 3-methylpentyl group, a 2-methylpentyl group, a 1-methylpentyl group, a heptyl group, an octyl group, an isooctyl group, a 2-ethylhexyl group, a 3,7-dimethyloctyl group, a nonyl group, a decyl group, an undecyl group, a dodecyl group, a tetradecyl group, a hexadecyl group, an octadecyl group, an eicosyl group and the like; and cycloalkyl groups such as a cyclopentyl group, a cyclohexyl group, an adamantyl group and the like.

Specific examples of the alkyl group substituted with a halogen atom, among optionally substituted alkyl groups, include a 2,2,2-trifluoroethyl group, a 3,3,3-trifluoropropyl group, a 4,4,4-trifluorobutyl group, a 5,5,5-trifluoropentyl group, a 6,6,6-trifluorohexyl group, a 7,7,7-trifluoroheptyl group, a 8,8,8-trifluorooctyl group, a 9,9,9-trifluorononyl group and a 10,10,10-trifluorodecyl group.

The optionally substituted alkoxy group may be linear or branched, and may also be a cycloalkoxy group. The substituent which the alkoxy group may have includes, for example, a halogen atom. Specific examples of the halogen atom are the same as specific examples of the halogen atom represented by R. The number of carbon atoms of the alkoxy group is usually about 1 to 20. The optionally substituted alkoxy group includes alkoxy groups in which a part of methylene groups is substituted with an oxygen atom.

Specific examples of the optionally substituted alkoxy group include a methoxy group, an ethoxy group, a propoxy group, an isopropoxy group, a butoxy group, an isobutoxy group, a tert-butoxy group, a pentyloxy group, a hexyloxy group, a cyclohexyloxy group, a heptyloxy group, an octyloxy group, a 2-ethylhexyloxy group, a nonyloxy group, a decyloxy group, a 3,7-dimethyloctyloxy group, a lauryloxy group, a trifluoromethoxy group, a pentafluoroethoxy group, a perfluorobutoxy group, a perfluorohexyloxy group, a perfluorooctyloxy group, a methoxymethyloxy group and a 2-methoxyethyloxy group.

The optionally substituted alkylthio group may be linear or branched, and may also be a cycloalkylthio group. The substituent which the alkylthio group may have includes, for example, a halogen atom. Specific examples of the halogen atom are the same as specific examples of the halogen atom represented by R. The number of carbon atoms of the alkylthio group is usually about 1 to 20. Specific examples of the optionally substituted alkylthio group include a methylthio group, an ethylthio group, a propylthio group, an isopropylthio group, a butylthio group, an isobutylthio group, a ter-butylthio group, a pentylthio group, a hexylthio group, a cyclohexylthio group, a heptylthio group, an octylthio group, a 2-ethylhexylthio group, a nonylthio group, a decylthio group, a 3,7-dimethyloctylthio group, a laurylthio group and a trifluoromethylthio group.

The aryl group is an atomic group obtained by removing from an optionally substituted aromatic hydrocarbon one hydrogen atom on the aromatic ring, and the number of carbon atoms thereof is usually 6 to 60. The substituent includes, for example, a halogen atom, an optionally substituted alkoxy group and an optionally substituted alkylthio group. Specific examples of the halogen atom, the optionally substituted alkoxy group and the optionally substituted alkylthio group are the same as specific examples of the halogen atom, the optionally substituted alkyl group, the optionally substituted alkoxy group and the optionally substituted alkylthio group represented by R. Specific examples of the aryl group include a phenyl group, C1 to C12 alkyloxyphenyl groups (The C1 to C12 alkyl denotes an alkyl having 1 to 12 carbon atoms. The C1 to C12 alkyl is preferably a C1 to C8 alkyl, more preferably a C1 to C6 alkyl. The C1 to C8 alkyl denote an alkyl having 1 to 8 carbon atoms, and the C1 to C6 alkyl denote an alkyl having 1 to 6 carbon atoms. Specific examples of the C1 to C12 alkyl, the C1 to C8 alkyl and the C1 to C6 alkyl include those explained and exemplified for the above-described alkyl group. The same shall apply hereinafter.), C1 to C12 alkylphenyl groups, a 1-naphthyl group, a 2-naphthyl group and a pentafluorophenyl group.

The number of carbon atoms of the aryloxy group is usually about 6 to 60. Specific examples of the aryloxy group include a phenoxy group, C1 to C12 alkyloxyphenoxy groups, C1 to C12 alkylphenoxy groups, a 1-naphthyloxy group, a 2-naphthyloxy group and a pentafluorophenyloxy group.

The number of carbon atoms of the arylthio group is usually about 6 to 60. Specific examples of the arylthio group include a phenylthio group, C1 to C12 alkyloxyphenylthio groups, C1 to C12 alkylphenylthio groups, a 1-naphthylthio group, a 2-naphthylthio group and a pentafluorophenylthio group.

The optionally substituted arylalkyl group has a number of carbon atoms of usually about 7 to 60, and the alkyl portion may have a substituent. The substituent includes, for example, a halogen atom. Specific examples of the halogen atom are the same as specific examples of the halogen atom represented by R. Specific examples of the optionally substituted arylalkyl group include phenyl C1 to C12 alkyl groups, C1 to C12 alkyloxyphenyl C1 to C12 alkyl groups, C1 to C12 alkylphenyl C1 to C12 alkyl groups, 1-naphthyl C1 to C12 alkyl groups and 2-naphthyl C1 to C12 alkyl groups.

The optionally substituted arylalkoxy group has a number of carbon atoms of usually about 7 to 60, and the alkoxy portion may have a substituent. The substituent includes, for example, a halogen atom. Specific examples of the halogen atom are the same as specific examples of the halogen atom represented by R. Specific examples of the optionally substituted arylalkyloxy group include phenyl C1 to C12 alkyloxy groups, C1 to C12 alkyloxyphenyl C1 to C12 alkyloxy groups, C1 to C12 alkylphenyl C1 to C12 alkyloxy groups, 1-naphthyl C1 to C12 alkyloxy groups and 2-naphthyl C1 to C12 alkyloxy groups.

The optionally substituted arylalkylthio group has a number of carbon atoms of usually about 7 to 60, and the alkylthio portion may have a substituent. The substituent includes, for example, a halogen atom. Specific examples of the halogen atom are the same as specific examples of the halogen atom represented by R. Specific examples of the optionally substituted arylalkylthio group include phenyl C1 to C12 alkylthio groups, C1 to C12 alkyloxyphenyl C1 to C12 alkylthio groups, C1 to C12 alkylphenyl C1 to C12 alkylthio groups, 1-naphthyl C1 to C12 alkylthio groups and 2-naphthyl C1 to C12 alkylthio groups.

The optionally substituted acyl group has a number of carbon atoms of usually about 2 to 20. The substituent which the acyl group may have includes, for example, a halogen atom. Specific examples of the halogen atom are the same as specific examples of the halogen atom represented by R. Specific examples of the optionally substituted acyl group include an acetyl group, a propionyl group, a butyryl group, an isobutyryl group, a pivaloyl group, a benzoyl group, a trifluoroacetyl group and a pentafluorobenzoyl group.

The optionally substituted acyloxy group has a number of carbon atoms of usually about 2 to 20. The substituent which the acyloxy group may have includes, for example, a halogen atom. Specific examples of the halogen atom are the same as specific examples of the halogen atom represented by R. Specific examples of the optionally substituted acyloxy group include an acetoxy group, a propionyloxy group, a butyryloxy group, an isobutyryloxy group, a pivaloyloxy group, a benzoyloxy group, a trifluoroacetyloxy group and a pentafluorobenzoyloxy group.

The optionally substituted amide group has a number of carbon atoms of usually about 1 to 20. The amide group denotes a group obtained by removing from an amide a hydrogen atom linked to its nitrogen atom. The substituent which the amide group may have includes, for example, a halogen atom. Specific examples of the halogen atom are the same as specific examples of the halogen atom represented by R. Specific examples of the optionally substituted amide group include a formamide group, an acetamide group, a propioamide group, a butyroamide group, a benzamide group, a trifluoroacetamide group, a pentafluorobenzamide group, a diformamide group, a diacetamide group, a dipropioamide group, a dibutyroamide group, a dibenzamide group, a ditrifluoroacetamide group and a dipentafluorobenzamide group.

The optionally substituted acid imide group denotes a group obtained by removing from an acid imide a hydrogen atom linked to its nitrogen atom. The acid imide group has a number of carbon atoms of usually about 2 to 20. The substituent which the acid imide group may have includes, for example, a halogen atom. Specific examples of the halogen atom are the same as specific examples of the halogen atom represented by R. Specific examples of the optionally substituted acid imide group include a succinimide group and a phthalic imide group.

The substituted amino group has a number of carbon atoms of usually about 1 to 40. The substituent which the substituted amino group has includes, for example, an optionally substituted alkyl group and an aryl group. Specific examples of the optionally substituted alkyl group and the aryl group are the same as specific examples of the optionally substituted alkyl group and the aryl group represented by R. Specific examples of the substituted amino group include a methylamino group, a dimethylamino group, an ethylamino group, a diethylamino group, a propylamino group, a dipropylamino group, an isopropylamino group, a diisopropylamino group, a butylamino group, an isobutylamino group, a ter-butylamino group, a pentylamino group, a hexylamino group, a cyclohexylamino group, a heptylamino group, an octylamino group, a 2-ethylhexylamino group, a nonylamino group, a decylamino group, a 3,7-dimethyloctylamino group, a laurylamino group, a cyclopentylamino group, a dicyclopentylamino group, a cyclohexylamino group, a dicyclohexylamino group, a pyrrolidyl group, a piperidyl group, a ditrifluoromethylamino group, a phenylamino group, a diphenylamino group, C1 to C12 alkoxyoxyphenylamino groups, di(C1 to C12 alkyloxyphenyl)amino groups, di(C1 to C12 alkylphenyl)amino groups, a 1-naphthylamino group, a 2-naphthylamino group, a pentafluorophenylamino group, a pyridylamino group, a pyridazinylamino group, a pyrimidylamino group, a pyrazylamino group, a triazylamino group, phenyl C1 to C12 alkylamino groups, C1 to C12 alkyloxyphenyl C1 to C12 alkylamino groups, C1 to C12 alkylphenyl C1 to C12 alkylamino groups, di(C1 to C12 alkyloxyphenyl C1 to C12 alkyl)amino groups, di(C1 to C12 alkylphenyl C1 to C12 alkyl)amino groups, 1-naphthyl C1 to C12 alkylamino groups and 2-naphthyl C1 to C12 alkylamino groups.

The substituted silyl group has a number of carbon atoms of usually about 3 to 40.

The substituent which the substituted silyl group has includes, for example, an optionally substituted alkyl group and an aryl group. Specific examples of the optionally substituted alkyl group and the aryl group are the same as specific examples of the optionally substituted alkyl group and the aryl group represented by R. Specific examples of the substituted silyl group include a trimethylsilyl group, a triethylsilyl group, a tripropylsilyl group, a triisopropylsilyl group, a ter-butyldimethylsilyl group, a triphenylsilyl group, a tri-p-xylylsilyl group, a tribenzylsilyl group, a diphenylmethylsilyl group, a ter-butyldiphenylsilyl group and a dimethylphenylsilyl group.

The substituted silyloxy group has a number of carbon atoms of usually about 3 to 40.

The substituent which the substituted silyloxy group has includes, for example, an optionally substituted alkyl group and an aryl group. Specific examples of the optionally substituted alkyl group and the aryl group are the same as specific examples of the optionally substituted alkyl group and the aryl group represented by R. Specific examples of the substituted silyloxy group include a trimethylsilyloxy group, a triethylsilyloxy group, a tripropylsilyloxy group, a triisopropylsilyloxy group, a ter-butyldimethylsilyloxy group, a triphenylsilyloxy group, a tri-p-xylylsilyloxy group, a tribenzylsilyloxy group, a diphenylmethylsilyloxy group, a ter-butyldiphenylsilyloxy group and a dimethylphenylsilyloxy group.

The substituted silylthio group has a number of carbon atoms of usually about 3 to 40.

The substituent which the substituted silylthio group has includes, for example, an optionally substituted alkyl group and an aryl group. Specific examples of the optionally substituted alkyl group and the aryl group are the same as specific examples of the optionally substituted alkyl group and the aryl group represented by R. Specific examples of the substituted silylthio group include a trimethylsilylthio group, a triethylsilylthio group, a tripropylsilylthio group, a triisopropylsilylthio group, a ter-butyldimethylsilylthio group, a triphenylsilylthio group, a tri-p-xylylsilylthio group, a tribenzylsilylthio group, a diphenylmethylsilylthio group, a ter-butyldiphenylsilylthio group and a dimethylphenylsilylthio group.

The substituted silylamino group has a number of carbon atoms of usually about 3 to 80, preferably 6 to 60.

The substituent which the substituted silylamino group has includes, for example, an optionally substituted alkyl group and an aryl group. Specific examples of the optionally substituted alkyl group and the aryl group are the same as specific examples of the optionally substituted alkyl group and the aryl group represented by R. Specific examples of the substituted silylamino group include a trimethylsilylamino group, a triethylsilylamino group, a tripropylsilylamino group, a triisopropylsilylamino group, a ter-butyldimethylsilylamino group, a triphenylsilylamino group, a tri-p-xylylsilylamino group, a tribenzylsilylamino group, a diphenylmethylsilylamino group, a ter-butyldiphenylsilylamino group, a dimethylphenylsilylamino group, a di(trimethylsilyl)amino group, a di(triethylsilyl)amino group, a di(tripropylsilyl)amino group, a di(triisopropylsilyl)amino group, a di(ter-butyldimethylsilyl)amino group, a di(triphenylsilyl)amino group, a di(tri-p-xylylsilyl)amino group, a di(tribenzylsilyl)amino group, a di(diphenylmethylsilyl)amino group, a di(ter-butyldiphenylsilyl)amino group and a di(dimethylphenylsilyl)amino group.

The monovalent heterocyclic group denotes an atomic group obtained by removing from an optionally substituted heterocyclic compound one hydrogen atom on the heterocyclic ring. The heterocyclic compound has a number of carbon atoms of usually about 4 to 20. The heterocyclic compound includes, for example, furan, thiophene, pyrrole, pyrroline, pyrrolidine, oxazole, isooxazole, thiazole, isothiazole, imidazole, imidazoline, imidazolidine, pyrazole, pyrazoline, pyrazolidine, furazan, triazole, thiadiazole, oxadiazole, tetrazole, pyran, pyridine, piperidine, thiopyran, pyridazine, pyrimidine, pyrazine, piperazine, morpholine, triazine, benzofuran, isobenzofuran, benzothiophene, indole, isoindole, indolizine, indoline, isoindoline, chromene, chromane, isochromane, benzopyran, quinoline, isoquinoline, quinolidine, benzoimidazole, benzothiazole, indazole, naphthyridine, quinoxaline, quinazoline, quinazolidine, cinnoline, phthalazine, purine, pteridine, carbazole, xanthene, phenanthridine, acridine, β-carboline, perimidine, phenanthroline, thianthrene, phenoxathiin, phenoxazine, phenothiazine and phenazine. The substituent which the heterocyclic compound may have includes, for example, a halogen atom, an optionally substituted alkyl group, an optionally substituted alkoxy group and an optionally substituted alkylthio group. Specific examples of the halogen atom, the optionally substituted alkyl group, the optionally substituted alkoxy group and the substituted and optionally substituted alkylthio groups are the same as specific examples of the halogen atom, the optionally substituted alkyl group, the optionally substituted alkoxy group and the optionally substituted alkylthio group represented by R. As the monovalent heterocyclic group, monovalent aromatic heterocyclic groups are preferable.

The heterocyclic oxy group includes a group represented by the formula (A-1) in which an oxygen atom is linked to a monovalent heterocyclic group.

The heterocyclic thio group includes a group represented by the formula (A-2) in which a sulfur atom is linked to a monovalent heterocyclic group.

$Ar^3$—O—　　　　　　　　　　　　　　　　(A-1)

$Ar^3$—S—　　　　　　　　　　　　　　　　(A-2)

(In the formulae (A-1) and (A-2), $Ar^3$ represents a monovalent heterocyclic group.)

Specific examples of the heterocyclic oxy group include a thienyloxy group, C1 to C12 alkylthienyloxy groups, a pyrrolyloxy group, a furyloxy group, a pyridyloxy group, C1 to C12 alkylpyridyloxy groups, an imidazolyloxy group, a pyrazolyloxy group, a triazolyloxy group, an oxazolyloxy group, a thiazoleoxy group and a thiadiazoleoxy group.

Specific examples of the heterocyclic thio group include a thienylmercapto group, C1 to C12 alkylthienylmercapto groups, a pyrrolylmercapto group, a furylmercapto group, a pyridylmercapto group, C1 to C12 alkylpyridylmercapto groups, an imidazolylmercapto group, a pyrazolylmercapto group, a triazolylmercapto group, an oxazolylmercapto group, a thiazolemercapto group and a thiadiazolemercapto group.

The arylalkenyl group has a number of carbon atoms of usually 8 to 20. The arylalkenyl group includes, specifically, a styryl group.

The arylalkynyl group has a number of carbon atoms of usually 8 to 20. The arylalkynyl group includes, specifically, a phenylacetylenyl group.

From the standpoint of enhancement of solubility in a solvent of a polymer compound synthesized using the reactive compound of the present invention (hereinafter, this polymer compound is called the polymer compound of the present invention), it is preferable that R represents an alkyl group having 6 or more carbon atoms (preferably, 6 to 20 carbon atoms), an alkoxy group having 6 or more carbon atoms (preferably, 6 to 20 carbon atoms), an alkylthio group having 6 or more carbon atoms, an aryl group, an aryloxy group, an arylthio group, an arylalkyl group, an arylalkyloxy group, an arylalkylthio group, an acyl group having 6 or more carbon atoms (preferably, 6 to 20 carbon atoms) and an acyloxy group having 6 or more carbon atoms (preferably, 6 to 20 carbon atoms), more preferably, an alkyl group having 6 or more carbon atoms, an alkoxy group having 6 or more carbon atoms, an aryl group and an aryloxy group, further preferably, an alkyl group having 6 or more carbon atoms.

The alkyl group having 6 or more carbon atoms as one preferable embodiment of R includes linear alkyl groups such as a hexyl group, a heptyl group, an octyl group, a nonyl group, a decyl group, an undecyl group, a dodecyl group, a tridecyl group, a tetradecyl group, a pentadecyl group, a hexadecyl group, a heptadecyl group, an octadecyl group, a nonadecyl group, an icosyl group, a triacontyl group, a tetracontyl group, a pentacontyl group and the like, and branched alkyl groups such as a 1,1,3,3-tetramethylbutyl group, a 1-methylheptyl group, a 2-ethylhexyl group, a 3,7-dimethyloctyl group, a 1-propylpentyl group, a 3-heptyldodecyl group, a 2-heptylundecyl group, a 2-octyldodecyl group, a 3,7,11-trimethyldodecyl group, a 3,7,11,15-tetramethylhexadecyl group, a 3,5,5-trimethylhexyl group and the like.

The alkyl group having 6 or more carbon atoms is selected appropriately in view of solubility in a solvent of the polymer compound of the present invention, and preferable are a hexyl group, a heptyl group, an octyl group, a nonyl group, a decyl group, an undecyl group, a dodecyl group, a tridecyl group, a tetradecyl group, a pentadecyl group, a hexadecyl group, a 2-ethylhexyl group, a 3,7-dimethyloctyl group, a 1-propylpentyl group and a 3-heptyldodecyl group, more preferable are a hexyl group, a heptyl group, an octyl group, a dodecyl group, a tetradecyl group, a hexadecyl group, a 2-ethylhexyl group, a 3,7-dimethyloctyl group and a 3-heptyldodecyl group, further preferable are a hexyl group, an octyl group, a dodecyl group, a hexadecyl group, a 2-ethylhexyl group, a 3,7-dimethyloctyl group and a 3-heptyldodecyl group.

As the aryl group as one preferable embodiment of R, a phenyl group substituted with an alkyl group is preferable if solubility in a solvent of the polymer compound of the present invention is taken into consideration. As the substitution position of the alkyl group, a para-position is preferable. The phenyl group substituted with an alkyl group at a para-position includes preferably a p-hexylphenyl group, a p-heptylphenyl group, a p-octylphenyl group, a p-nonylphenyl group, a p-decylphenyl group, a p-undecylphenyl group, a p-dodecylphenyl group, a p-tridecylphenyl group, a p-tetradecylphenyl group, a p-pentadecylphenyl group, a p-hexadecylphenyl group, a p-2-ethylhexylphenyl group, a p-3,7-dimethyloctylphenyl group, a p-1-propylpentylphenyl group and a p-2-hexyldecylphenyl group, more preferably a p-hexylphenyl group, a p-heptylphenyl group, a p-octylphenyl group, a p-dodecylphenyl group, a p-pentadecylphenyl group, a p-hexadecylphenyl group, a p-2-ethylhexylphenyl group, a p-3,7-dimethyloctylphenyl group and a p-2-hexyldecylphenyl group, particularly preferably a p-dodecylphenyl group, a p-pentadecylphenyl group, a p-2-ethylhexylphenyl group and a p-3,7-dimethyloctylphenyl group.

In the formula (I), each of (monovalent) boronate residues having a hydroxyl group represented by Y situated at two positions has at least one hydroxyl group. The number of the hydroxyl group varies depending on the structure of the boronate residue, and is preferably 1 to 4, more preferably 1 to 2.

The boronate residue having a hydroxyl group includes boronate residues formed of a tri- or more-hydric alcohol and divalent boronic acid, and a group represented by the formula (A):

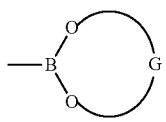

(A)

(Here, G represents a divalent saturated hydrocarbon group having at least one hydroxyl group.) is preferable.

The divalent saturated hydrocarbon group having at least one hydroxyl group has a number of carbon atoms of usually about 2 to 84, preferably 2 to 10.

Examples of the divalent saturated hydrocarbon group having at least one hydroxyl group include groups represented by (A-1) to (A-3).

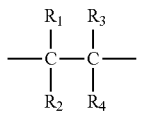

(A-1)

Here, $R_1$ to $R_4$ are the same or different from each other, and represent a hydrogen atom, a methyl group, an ethyl group, a substituent represented by the formula (R'-1), a substituent represented by the formula (R'-2) or a substituent represented by the formula (R'-3) described below. In the formula, one or more and four or less (preferably, one or more and two or less) of $R_1$ to $R_4$ are a group selected from the group consisting of a substituent represented by the formula (R'-1), a substituent represented by the formula (R'-2) and a substituent represented by the formula (R'-3) described below.

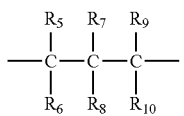

(A-2)

Here, $R_5$ to $R_{10}$ are the same or different from each other, and represent a hydrogen atom, a methyl group, an ethyl group, a substituent represented by the formula (R'-1), a substituent represented by the formula (R'-2) or a substituent represented by the formula (R'-3) described below. In the formula, one or more and six or less (preferably, one or more and four or less, more preferably, one or more and two or less) of $R_5$ to $R_{10}$ are a group selected from the group consisting of a substituent represented by the formula (R'-1), a substituent represented by the formula (R'-2) and a substituent represented by the formula (R'-3) described below.

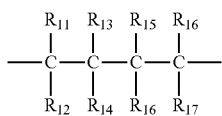

(A-3)

Here, $R_{11}$ to $R_{17}$ are the same or different from each other, and represent a hydrogen atom, a methyl group, an ethyl group, a substituent represented by the formula (R'-1), a substituent represented by the formula (R'-2) or a substituent represented by the formula (R'-3) described below. In the formula, one or more and eight or less (preferably, one or more and four or less, more preferably, one or more and two or less) of $R_{11}$ to $R_{17}$ are a group selected from the group consisting of a substituent represented by the formula (R'-1), a substituent represented by the formula (R'-2) and a substituent represented by the formula (R'-3) described below.

Particularly, groups represented by the following formulae (Y'-1) to (Y'-3) are more preferable.

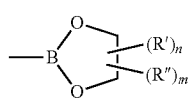

(Y'-1)

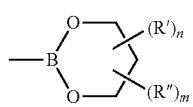

(Y'-2)

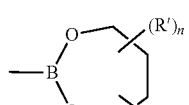

(Y'-3)

[In the formulae (Y'-1), (Y'-2) and (Y'-3), R' is a substituent represented by the following formula (R'-1), (R'-2) or (R'-3). R'' represents a hydrogen atom, a methyl group or an ethyl group. n and m each represent an integer, and satisfy n≥1, m≥0 and n+m≤4.]

When there are a plurality of R' in any of the formulae (Y'-1), (Y'-2) and (Y'-3), they may be the same or different.

When there are a plurality of R'' in any of the formulae (Y'-1), (Y'-2) and (Y'-3), they may be the same or different.

R' is a substituent containing a hydroxyl group.

R' is preferably a group represented by the following formulae (R'-1) to (R'-3).

(R'-1)

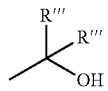

(R'-2)

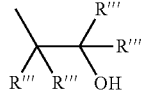

(R'-3)

[In the formulae (R'-1), (R'-2) and (R'-3), a plurality of R''' are the same or different from each other, and represent the same meaning as for R''. That is, R''' are the same or different from each other, and represent a hydrogen atom, a methyl group or an ethyl group.]

When there are a plurality of R''' in any of the formulae (R'-1), (R'-2) and (R'-3), they may be the same or different.

The boronate residues having a hydroxyl group represented by the formulae (Y'-1) to (Y'-3) are not particularly restricted, and the following formulae (Y-1) to (Y-16) are exemplified.

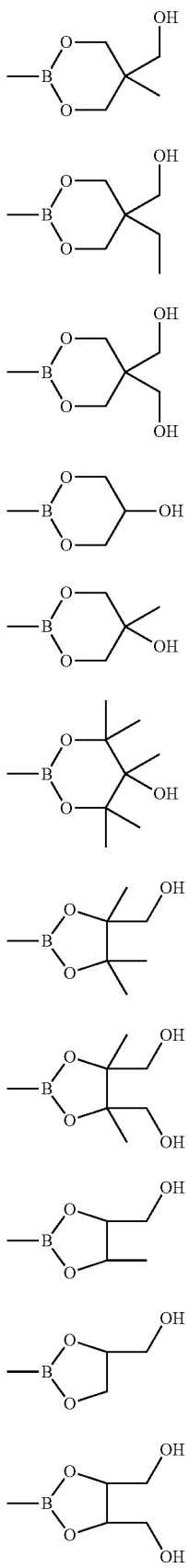

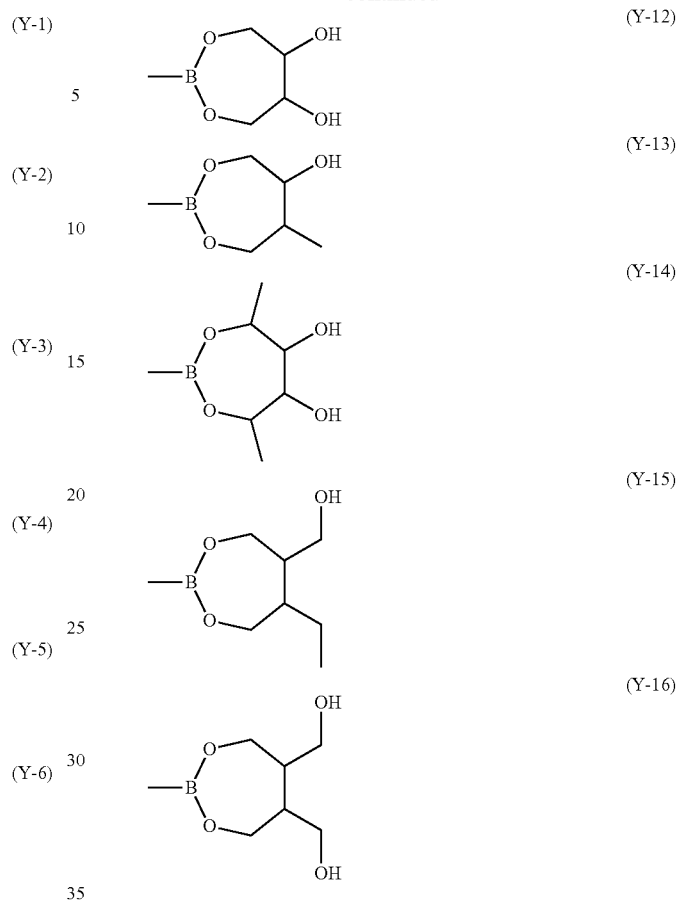

Of boronate residues having a hydroxyl group represented by the formulae (Y-1) to (Y-16), preferable are the formula (Y-1), the formula (Y-2), the formula (Y-3), the formula (Y-4), the formula (Y-10), the formula (Y-11) and the formula (Y-12), more preferable are the formula (Y-1), the formula (Y-2) and the formula (Y-3), further preferable is the formula (Y-1), from the standpoint of an improvement in the purity of the reactive compound.

$Ar^1$ and $Ar^2$ may be the same or different, and represent a trivalent aromatic hydrocarbon group or a trivalent heterocyclic group, preferably a trivalent heterocyclic group. Of trivalent heterocyclic groups, trivalent aromatic heterocyclic groups are more preferable.

The trivalent aromatic heterocyclic group represented by $Ar^1$ and $Ar^2$ denotes an atomic group remaining after removing from an optionally substituted heterocyclic compound having aromaticity three hydrogen atoms on the aromatic ring. The trivalent aromatic heterocyclic group has a number of carbon atoms of usually 2 to 60, preferably 4 to 60, more preferably 4 to 20.

The substituent which the heterocyclic compound having aromaticity may have includes, for example, a halogen atom and a monovalent group. Definitions and specific examples of the halogen atom and the monovalent group are the same as definitions and specific examples of the halogen atom and the monovalent group represented by R.

The trivalent heterocyclic group represented by Ar and $Ar^2$ includes, for example, groups represented by the formulae (201) to the (301).

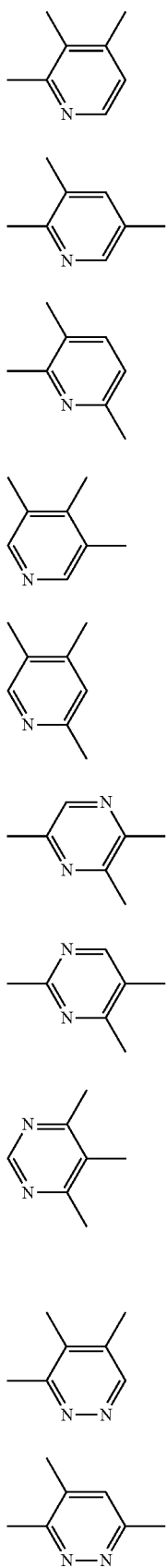
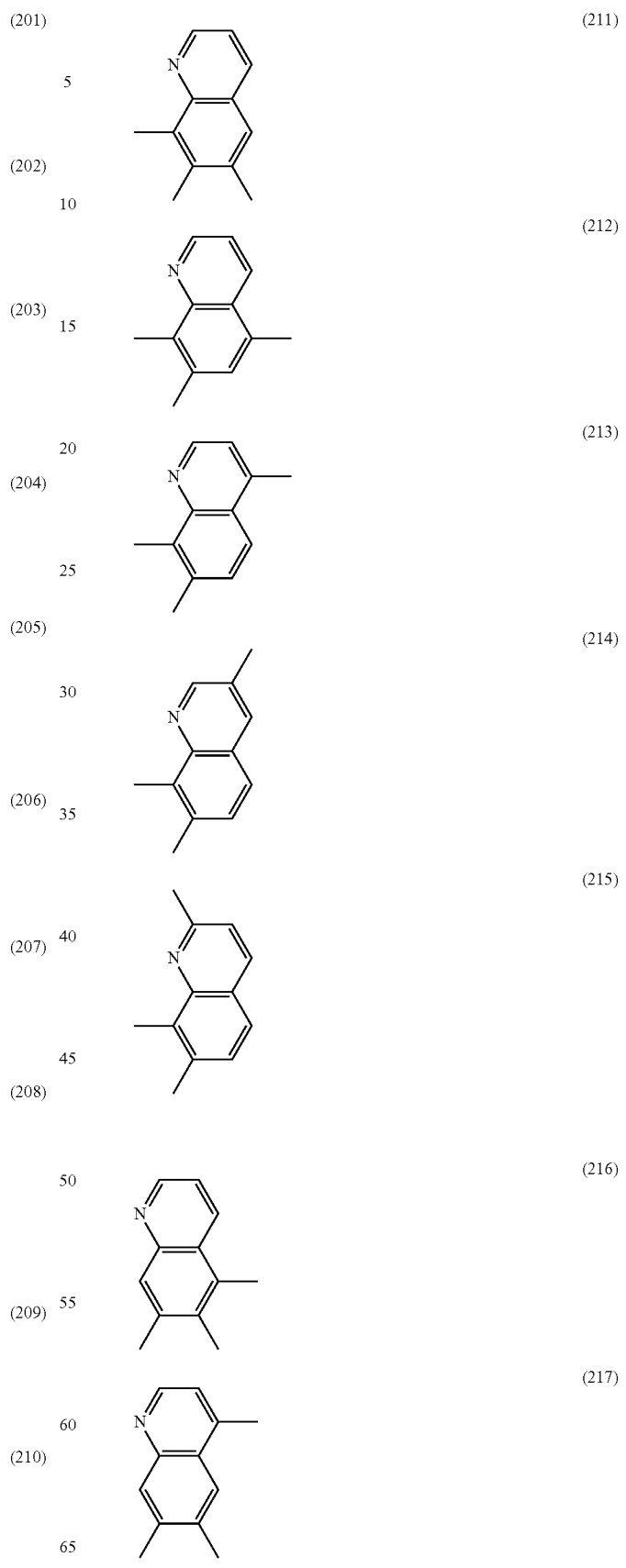

(218) 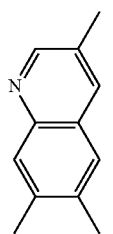
(219) 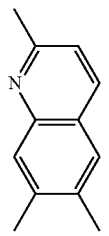
(220) 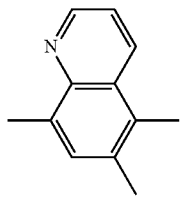
(221) 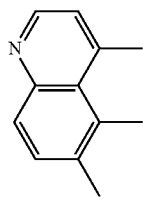
(222) 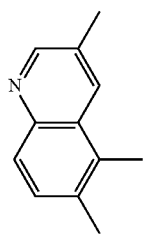
(223) 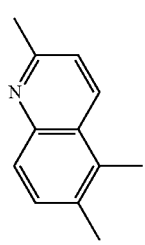
(224) 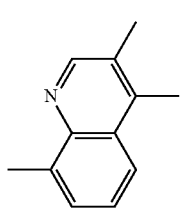
(225) 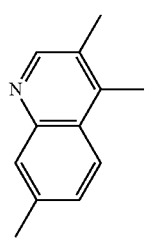
(226) 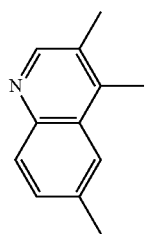
(227) 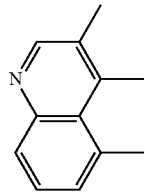
(228) 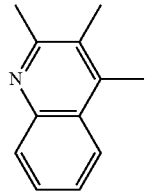
(229) 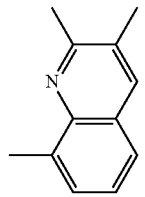
(230) 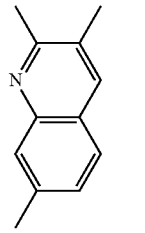
(231) 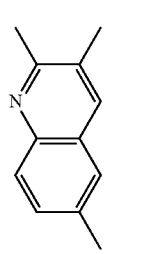

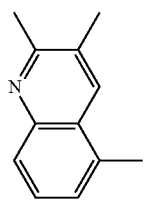 (232)
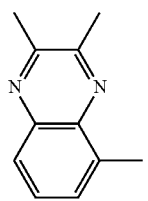 (233)
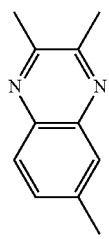 (234)
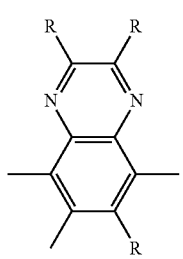 (235)
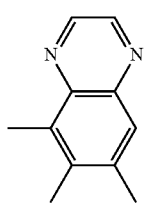 (236)
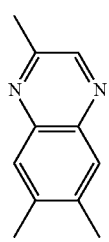 (237)
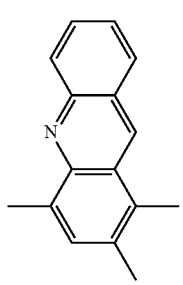 (238)
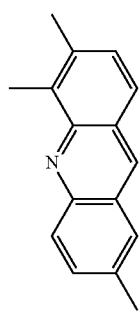 (239)
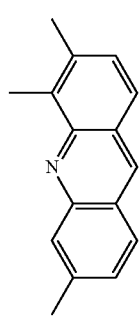 (240)
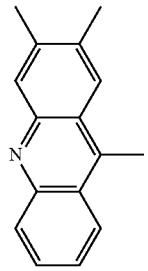 (241)
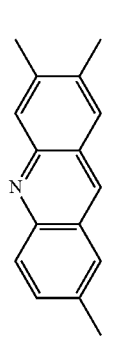 (242)
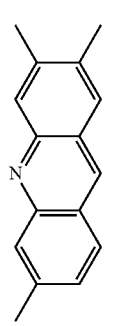 (243)

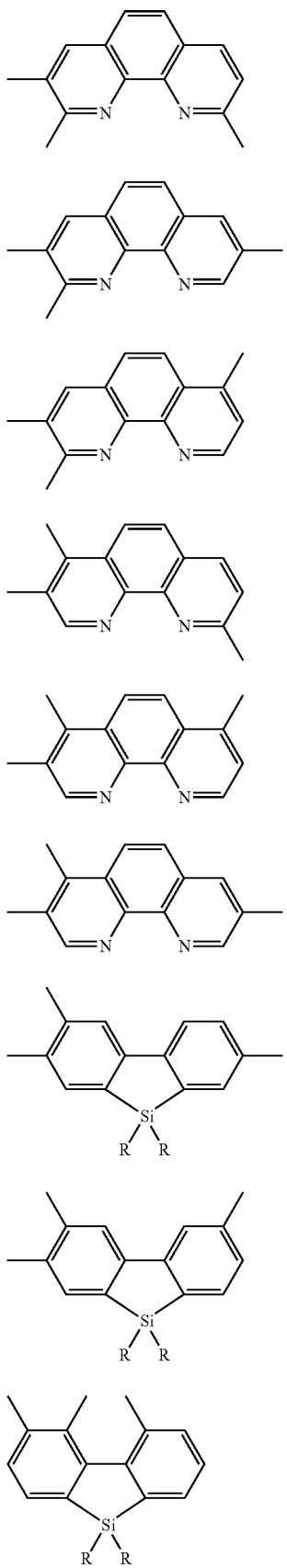
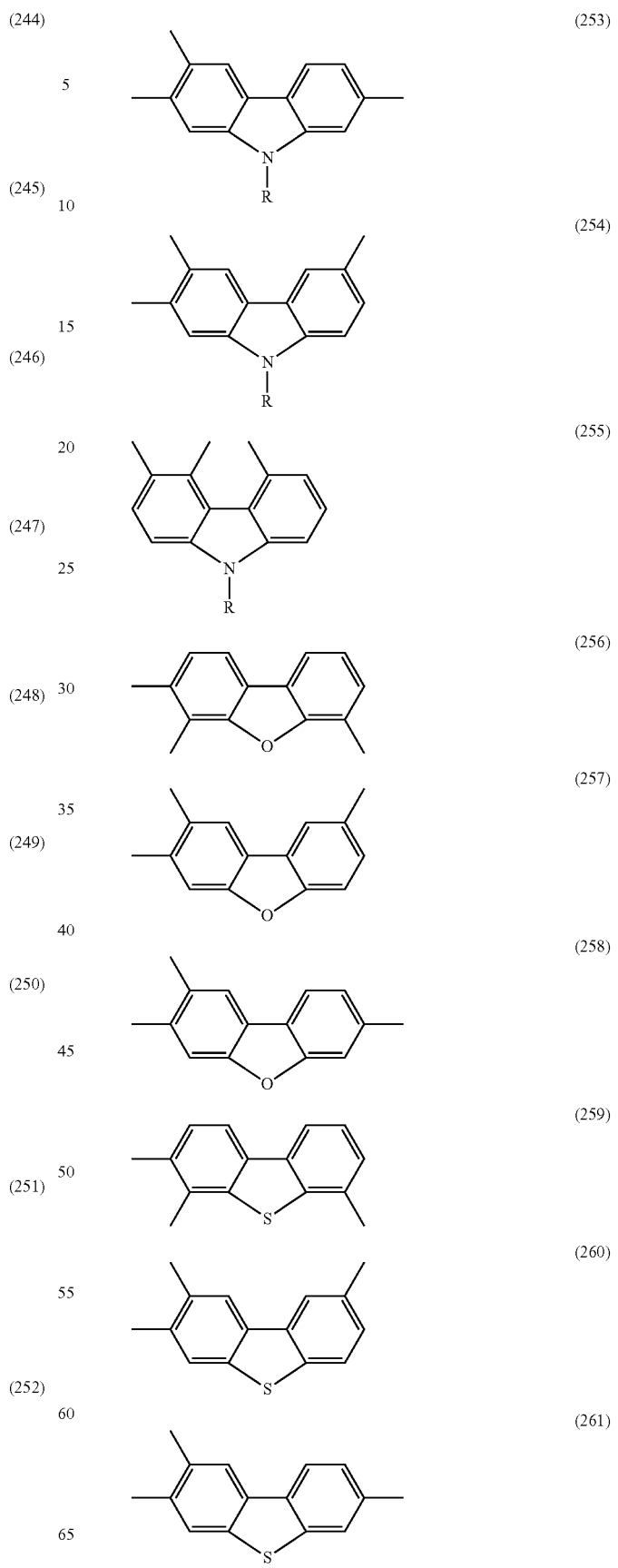

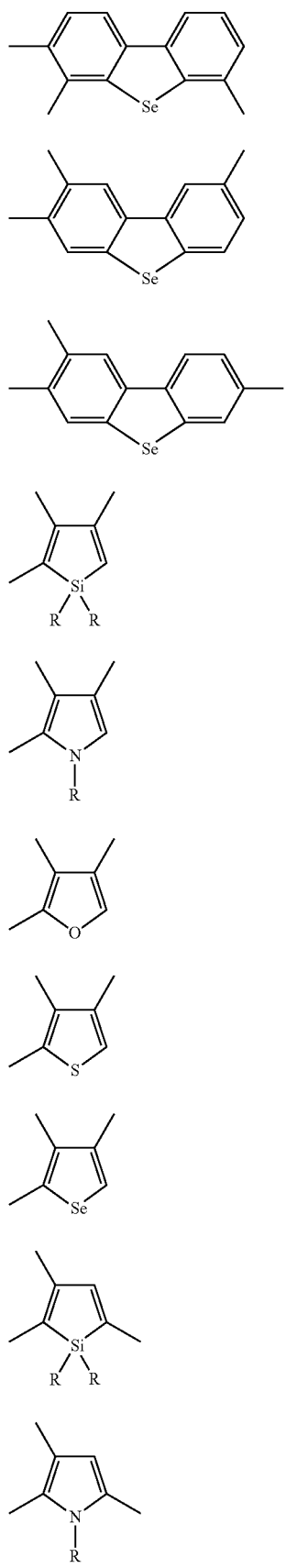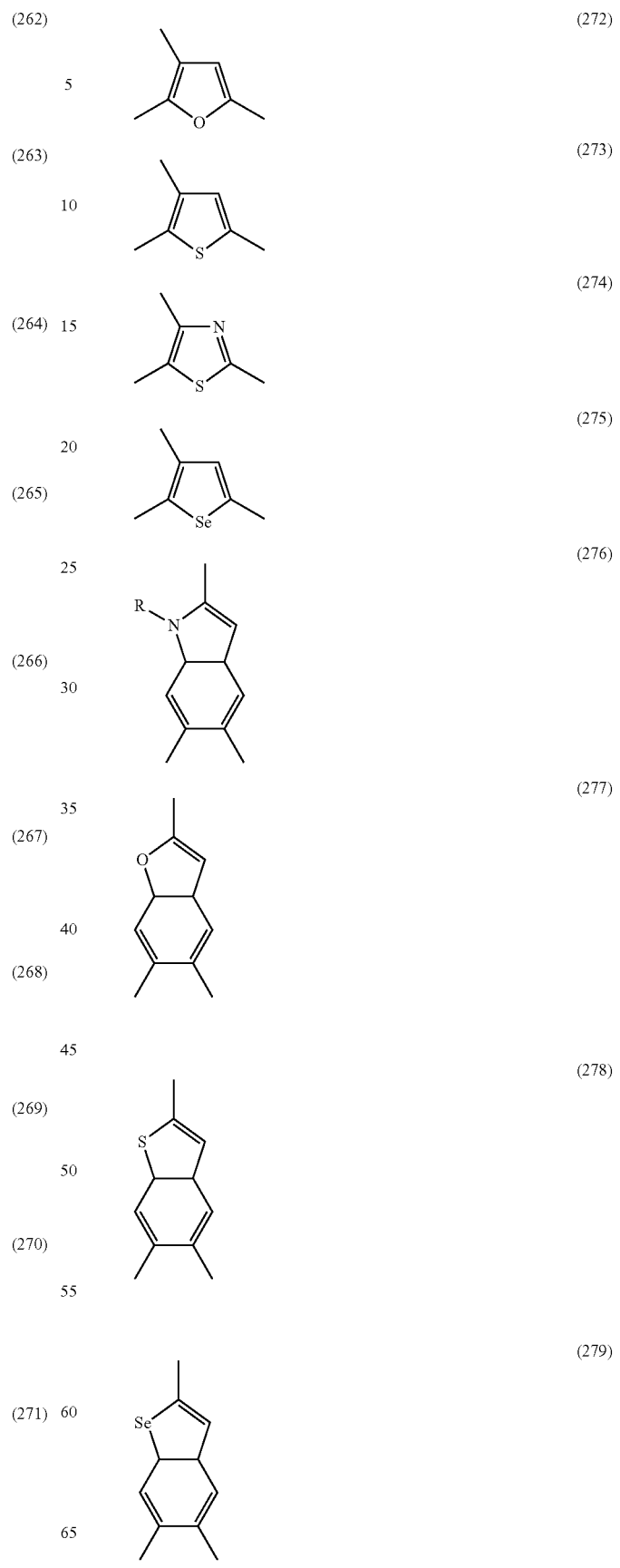

(280) 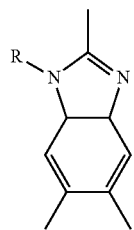
(281) 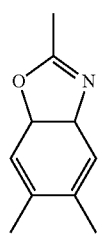
(282) 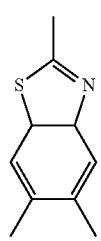
(283) 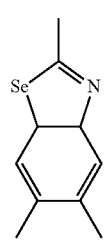
(284) 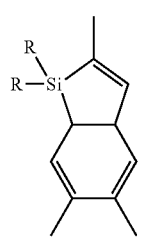
(285) 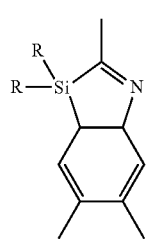
(286) 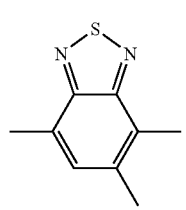
(287) 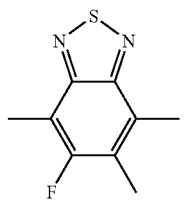
(288) 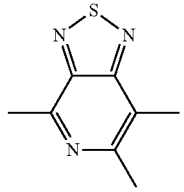
(289) 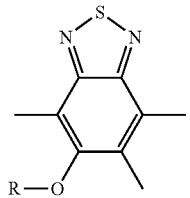
(290) 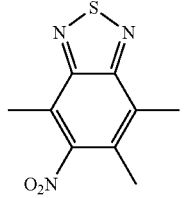
(291) 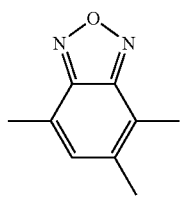
(292) 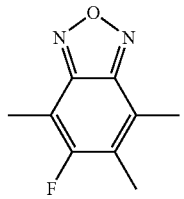
(293) 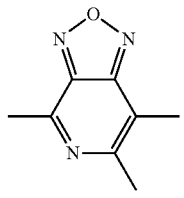

-continued (294) 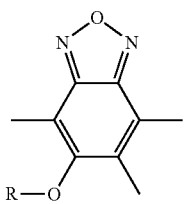

(295) 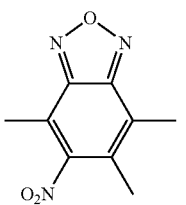

(296) 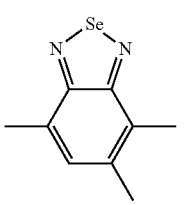

(297) 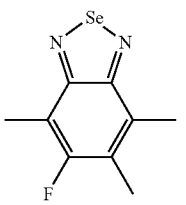

(298) 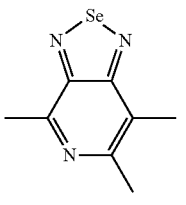

(299) 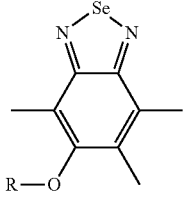

(300)

(301) 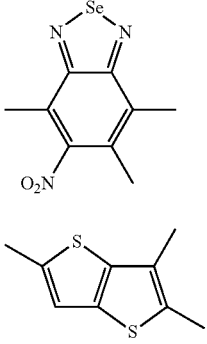

(In the formulae, R represents the same meaning as described above.)

The trivalent aromatic hydrocarbon group represented by $Ar^1$ and $Ar^2$ denotes an atomic group remaining after removing from an optionally substituted aromatic hydrocarbon three hydrogen atoms on the aromatic ring. The trivalent aromatic hydrocarbon group has a number of carbon atoms of usually 6 to 60, preferably 6 to 20.

The aromatic hydrocarbon includes also a compound containing a benzene ring, a compound containing a condensed ring, a compound having a structure containing two or more independent benzene rings or condensed rings linked directly and a compound containing two or more independent benzene rings or condensed rings linked via a group such as vinylene or the like.

The substituent which the aromatic hydrocarbon may have includes, for example, a halogen atom and a monovalent group. Definitions and specific examples of the halogen atom and the monovalent group are the same as definitions and specific examples of the halogen atom and the monovalent group represented by R.

The trivalent aromatic hydrocarbon group represented by $Ar^1$ and $Ar^2$ includes, for example, groups represented by the formulae (302) to (311).

(302) 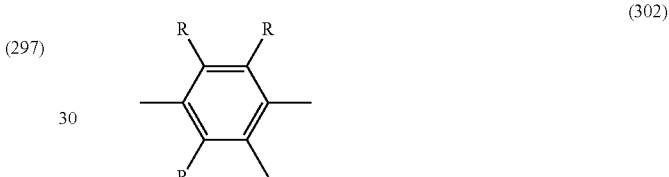

(303) 

(304) 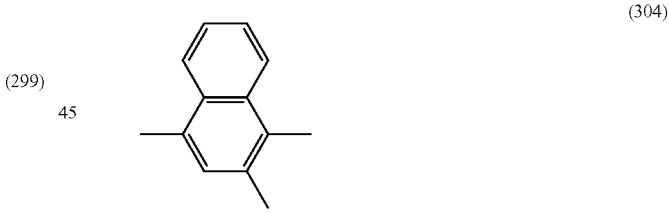

(305) 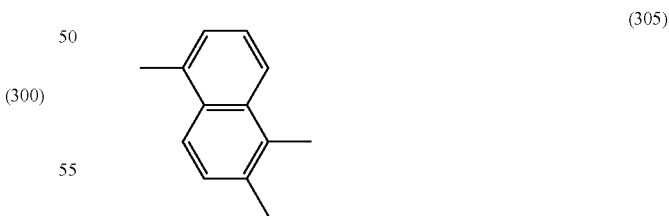

(306) 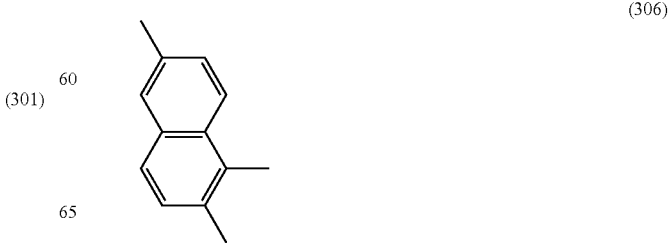

(307)

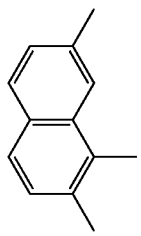

(308)

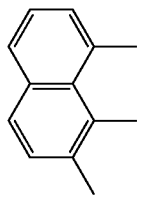

(309)

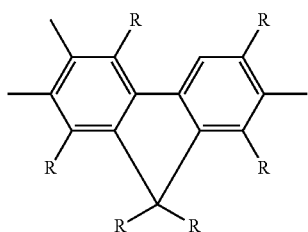

(310)

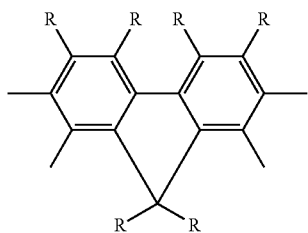

(311)

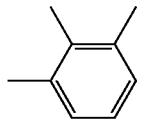

(In the formulae, R represents the same meaning as described above.)

Of groups represented by the formulae (201) to (311), groups represents the formula (202), the formula (205), the formula (206), the formula (207), the formula (210), the formula (212), the formula (220), the formula (235), the formula (238), the formula (270), the formula (271), the formula (272), the formula (273), the formula (274), the formula (275), the formula (286), the formula (287), the formula (288), the formula (291), the formula (292), the formula (293), the formula (296), the formula (301) and the formula (302) are preferable, groups represents the formula (235), the formula (271), the formula (272), the formula (273), the formula (274), the formula (286), the formula (291), the formula (296), the formula (301) and the formula (302) are more preferable, groups represented by the formula (271), the formula (272), the formula (273), the formula (274) and the formula (311) are further preferable, a group represented by the formula (273) is particularly preferable, from the standpoint of easiness of synthesis of the reactive compound of the present invention.

The reactive compound represented by the formula (I) is preferably a compound represented by the following for-mula (II), more preferably a compound represented by the following formula (III-1) or (III-2).

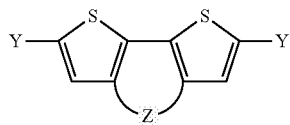

(II)

[In the formula (II), Z represents the same meaning as described above, and Y represents the same meaning as described above.]

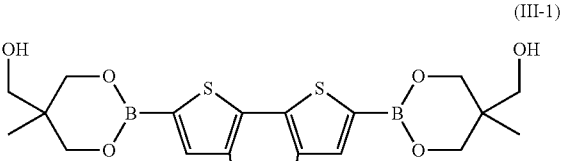

(III-1)

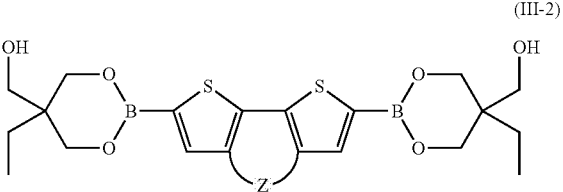

(III-2)

[In the formulae (III-1) and (III-2), Z represents the same meaning as described above.]

The reactive compound represented by the formula (II) includes, for example, compounds represented by the formulae (501) to (515).

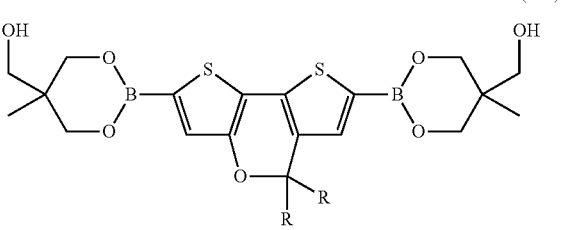

(501)

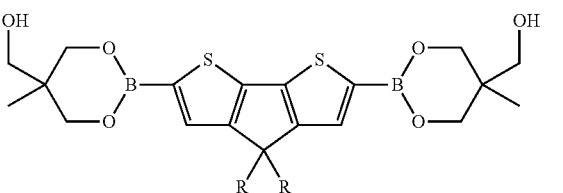

(502)

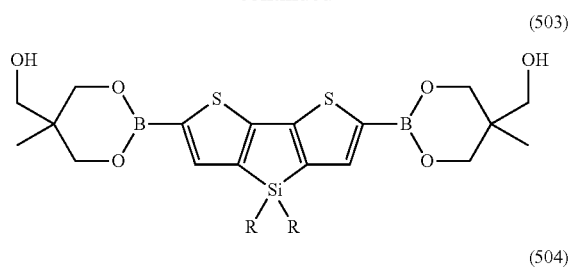
(503)

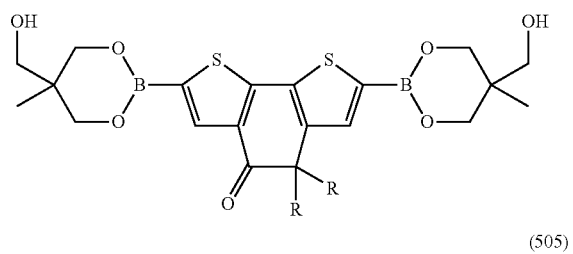
(504)

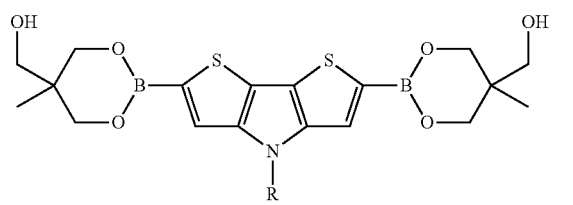
(505)

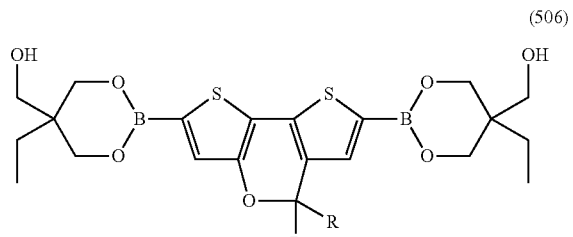
(506)

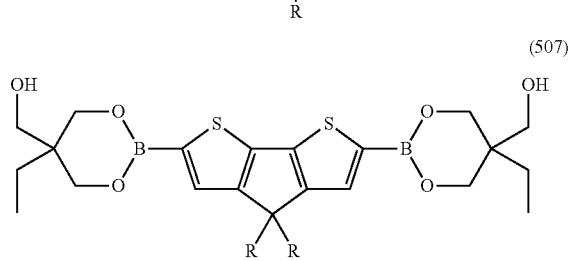
(507)

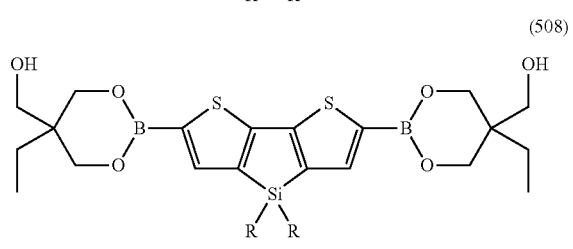
(508)

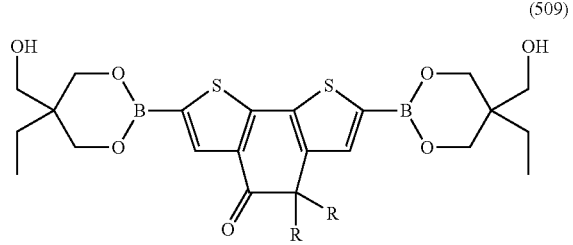
(509)

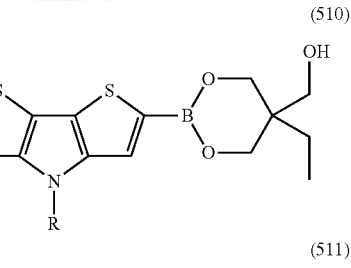
(510)

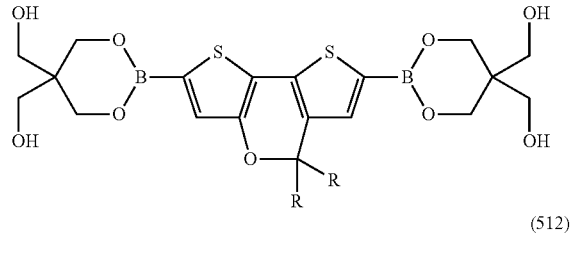
(511)

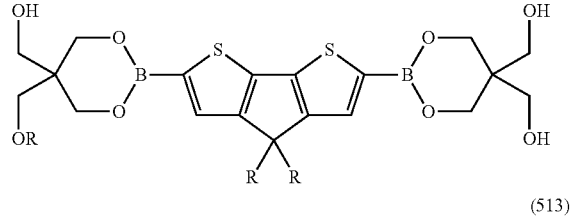
(512)

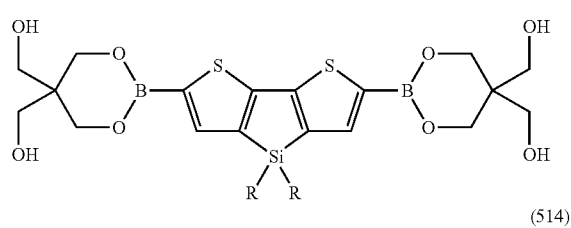
(513)

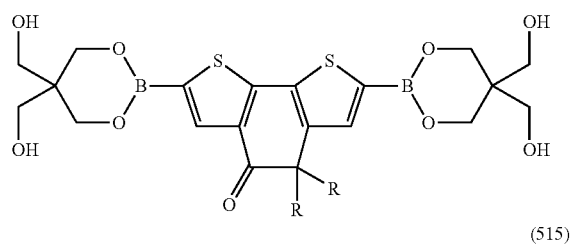
(514)

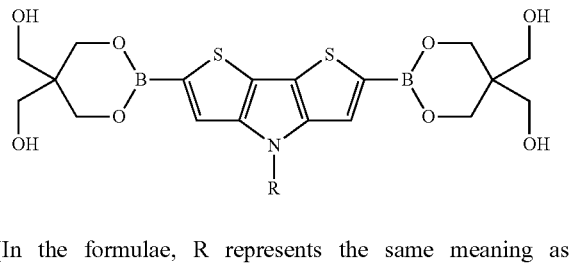
(515)

[In the formulae, R represents the same meaning as described above.]

Of compounds represented by the formulae (501) to (515) described above, compounds represented by the formula (501), the formula (502), the formula (503), the formula (504), the formula (505) and the formula (506) are preferable, compounds represented by the formula (501), the formula (502), the formula (503), the formula (504) and the formula (506) are more preferable, compounds represented by the formula (501), the formula (503) and the formula (506) are further preferable, compounds represented by the formula (501) and the formula (506) are particularly preferable, a compound represented by the formula (501) is especially preferable, from the standpoint of easiness of an improvement in the purity of the reactive compound of the present invention.

The purity of the reactive compound in the present invention denotes an area percentage value of a peak of the targeted compound according to high performance liquid chromatography. The purity of the reactive compound of the present invention is preferably 90% or more. When the purity is lower than 90%, the attainable molecular weight may stay low, and the intended electric property may not be manifested. The purity of the reactive compound is preferably 95% or more, more preferably 98% or more, further preferably 99% or more.

The polymer compound of the present invention has a weight average molecular weight of 1000 or more. The weight average molecular weight of the polymer compound of the present invention is preferably 3000 to 10000000. When the weight average molecular weight is smaller than 3000, a film formed in device fabrication may indicate defects generated, and when larger than 10000000, solubility in a solvent and coatability in device fabrication may lower. The weight average molecular weight of the polymer compound is more preferably 4000 to 5000000, further preferably 5000 to 1000000.

The weight average molecular weight in the present invention denotes a polystyrene-equivalent weight average molecular weight calculated using a standard sample of polystyrene, using gel permeation chromatography (GPC).

It is advantageous that at least one constituent unit obtained by removing "Y" on both ends from a compound represented by the formula (1) is contained in the polymer compound of the present invention. It is preferable that on average two or more constituent units are contained per one polymer chain, and it is further preferable that on average three or more constituent units are contained per one polymer chain.

When the polymer compound of the present invention is used in a device, it is desirable that solubility in a solvent of the polymer compound is high from the standpoint of easiness of device fabrication. Specifically, it is preferable that the polymer compound of the present invention has solubility by which a solution containing the polymer compound in an amount of 0.01 wt % or more can be prepared, more preferably, in an amount of 0.1 wt % or more, further preferably, in an amount of 0.2 wt % or more.

Though the method of producing the polymer compound of the present invention is not particularly restricted, a method using the Suzuki coupling reaction is preferable from the standpoint of easiness of synthesis of the polymer compound.

The method using the Suzuki coupling reaction includes, for example, a method of producing a polymer compound containing a constituent unit represented by the following formula (VI) and a constituent unit represented by the following formula (VII):

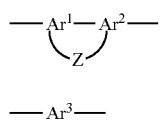

comprising reacting at least one compound represented by the formula (I):

[In the formula, $Ar^1$, $Ar^2$, Z and Y represent the same meaning as described above.]

and at least one compound represented by the formula (V):

$$X-Ar^3-X \qquad (V)$$

[In the formula, $Ar^3$ represents a divalent aromatic hydrocarbon group or a divalent heterocyclic group. In the formula, a plurality of X are the same or different from each other, and represent a halogen atom.].

The above-described reaction includes a production method carried out in the presence of a palladium catalyst and a base.

The divalent aromatic hydrocarbon group represented by $Ar^3$ in the formula denotes an atomic group obtained by removing from an optionally substituted aromatic hydrocarbon two hydrogen atoms on the aromatic ring. The divalent aromatic hydrocarbon group has a number of carbon atoms of usually about 6 to 60, preferably 6 to 20.

The substituent which the aromatic hydrocarbon may have includes, for example, a halogen atom or a monovalent group. Definitions and specific examples of the halogen atom and the monovalent group are the same as definitions and specific examples of the halogen atom and the monovalent group represented by R.

The divalent heterocyclic group represented by $Ar^3$ in the formula denotes an atomic group obtained by removing from an optionally substituted heterocyclic compound two hydrogen atoms on the heterocyclic ring. As the divalent heterocyclic group, divalent aromatic heterocyclic groups are preferable.

The substituent which the heterocyclic compound may have includes, for example, a halogen atom or a monovalent group. Definitions and specific examples of the halogen atom and the monovalent group are the same as definitions and specific examples of the halogen atom and the monovalent group represented by R.

As the divalent aromatic hydrocarbon group or the divalent heterocyclic group represented by $Ar^3$ in the formula, groups (constituent units) represented by the formulae (Cy-1) to (Cy-5) are preferable, from the standpoint of enhancement of photoelectric conversion efficiency of an organic film solar battery when the polymer compound of the present invention is used as an active layer of the organic film solar battery.

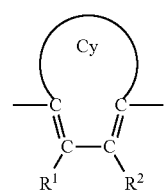

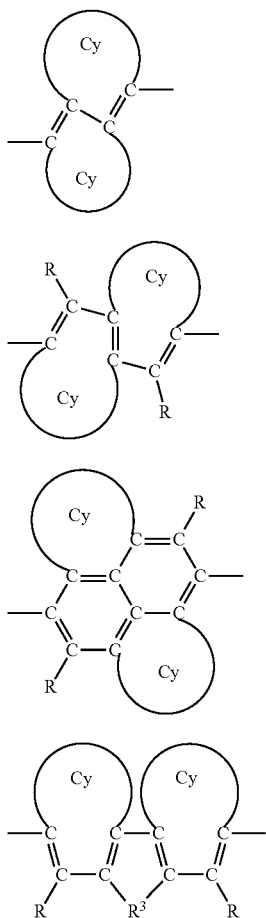

(Cy-2)

(Cy-3)

(Cy-4)

(Cy-5)

(In the formulae (Cy-1) to (Cy-5), R represents the same meaning as described above. $R^1$ and $R^2$ represent each independently a hydrogen atom, a halogen atom or a monovalent group. $R^1$ and $R^2$ may be mutually connected to form a cyclic structure together with a carbon atom to which they are linked. Rings Cy are the same or different from each other, and represent an optionally substituted aromatic ring. $R^3$ represents a divalent group.)

Definitions and specific examples of the halogen atom and the monovalent group represented by $R^1$ and $R^2$ are the same as definitions and specific examples of the halogen atom and the monovalent group represented by R.

$R^1$ and $R^2$ may be mutually connected to form a cyclic structure together with a carbon atom to which they are linked. Specific examples of the cyclic structure include structures represented by the formulae (D-1) to (D-5).

(D-1)

(D-2)

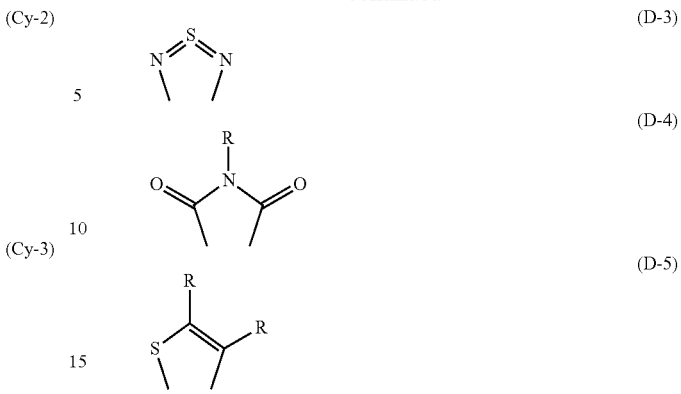

(D-3)

(D-4)

(D-5)

(In the formulae (D-1) to (D-5), R represents the same meaning as described above.)

The aromatic ring represents the ring Cy may be a single ring or a condensed ring. The aromatic ring in the form of a single ring includes, for example, a benzene ring, a pyrrole ring, a furan ring, a thiophene ring, an oxazole ring, a thiazole ring, a thiadiazole ring, a pyrazole ring, a pyridine ring, a pyrazine ring, an imidazole ring, a triazole ring, an isooxazole ring, an isothiazole ring, a pyrimidine ring, a pyridazine ring and a triazine ring.

The aromatic ring in the form of a condensed ring includes aromatic rings obtained by condensation of any rings to the above-described single rings. The ring to be condensed to the single ring includes, for example, a furan ring, a thiophene ring, a pyrrole ring, a pyrroline ring, a pyrrolidine ring, an oxazole ring, an isooxazole ring, a thiazole ring, an isothiazole ring, a thiadiazole ring, an imidazole ring, an imidazoline ring, an imidazolidine ring, a pyrazole ring, a pyrazoline ring, a pyrazolidine ring, a furazan ring, a triazole ring, a thiadiazole ring, an oxadiazole ring, a tetrazole ring, a pyran ring, a pyridine ring, a piperidine ring, a thiopyran ring, a pyridazine ring, a pyrimidine ring, a pyrazine ring, a piperazine ring, a morpholine ring, a triazine ring, a benzofuran ring, an isobenzofuran ring, a benzothiophene ring, an indole ring, an isoindole ring, an indolizine ring, an indoline ring, an isoindoline ring, a chromene ring, a chromane ring, an isochromane ring, a benzopyran ring, a quinoline ring, an isoquinoline ring, a quinolidine ring, a benzoimidazole ring, a benzothiazole ring, an indazole ring, a naphthyridine ring, a quinoxaline ring, a quinazoline ring, a quinazolidine ring, a cinnoline ring, a phthalazine ring, a purine ring, a pteridine ring, a carbazole ring, a xanthene ring, a phenanthridine ring, an acridine ring, a R-carboline ring, a pyrimidine ring, a phenanthroline ring, a thianthrene ring, a phenoxathiin ring, a phenoxazine ring, a phenothiazine ring and a phenazine ring.

The substituent which the aromatic ring may have in the ring Cy includes, for example, a halogen atom and a monovalent group. Definitions and specific examples of the halogen atom and the monovalent group are the same as definitions and specific examples of the halogen atom and the monovalent group represented by R.

Specific examples of the divalent group represented by $R^3$ include groups represented by the formulae (b-1) to (b-7).

(b-1)

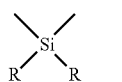 (b-2)
 (b-3)
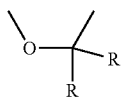 (b-4)
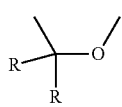 (b-5)
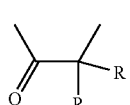 (b-6)
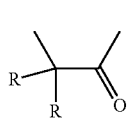 (b-7)
(In the formulae (b-1) to (b-7), R represents the same meaning as described above.)
The constituent unit represented by the formulae (Cy-1) to (Cy-5) includes, for example, constituent units represented by the formulae (C-1) to (C-31).
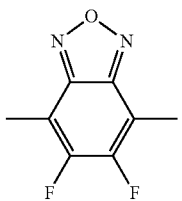 (C-1)
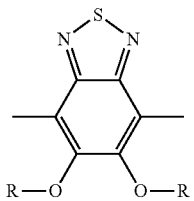 (C-2)
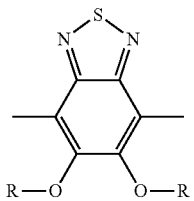 (C-3)
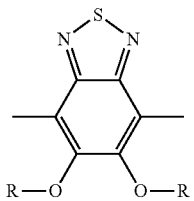 (C-4)
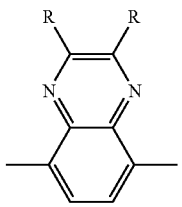 (C-5)
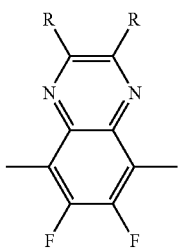 (C-6)
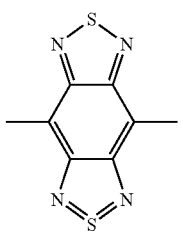 (C-7)
 (C-8)
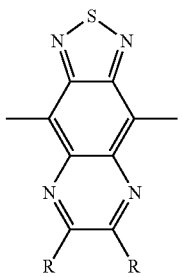 (C-9)

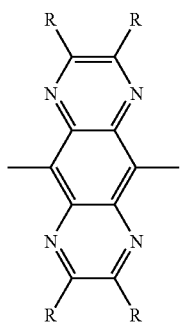 (C-10)
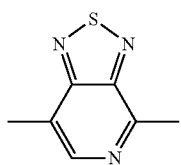 (C-11)
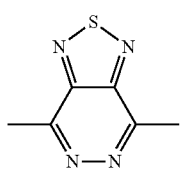 (C-12)
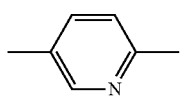 (C-13)
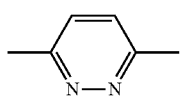 (C-14)
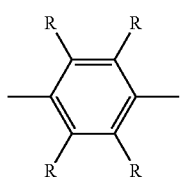 (C-15)
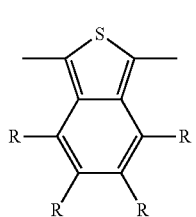 (C-16)
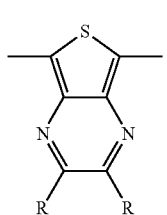 (C-17)
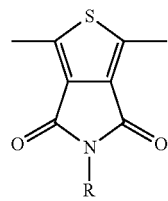 (C-18)
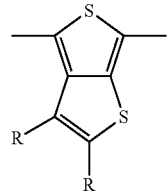 (C-19)
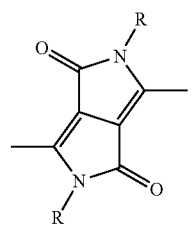 (C-20)
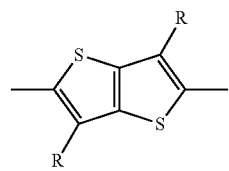 (C-21)
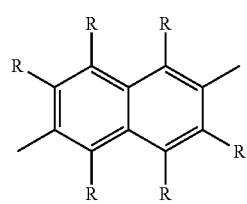 (C-22)
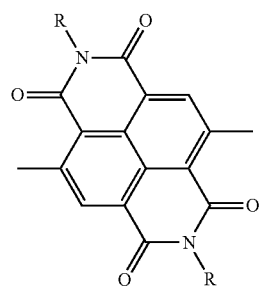 (C-23)
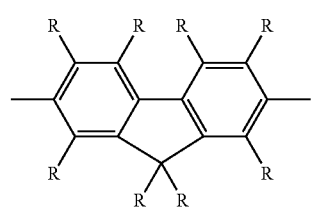 (C-24)

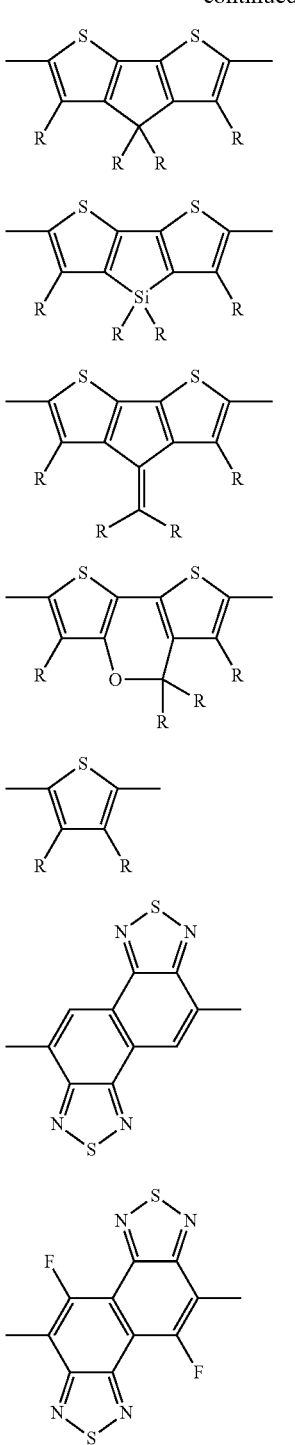

(In the formulae (C-1) to (C-29), R represents the same meaning as described above.)

When the compound of the present invention is used as a material of an organic film solar battery, the constituent unit represented by the formulae (C-30) and (C-31) includes preferably a constituent unit represented by the formula (C-3), from the standpoint of open end voltage.

When the compound of the present invention is used as a material of an organic film solar battery, the constituent unit represented by the formulae (C-1) to (C-5) includes prefer- ably constituent units represented by the formulae (C-2) and (C-3), particularly preferably a constituent unit represented by the formula (C-3), from the standpoint of open end voltage.

When the compound of the present invention is used as a material of an organic film solar battery, the constituent unit represented by the formula (C-15) includes preferably a constituent unit represented by the formula (C-32) and a constituent unit represented by the formula (C-33), from the standpoint of open end voltage.

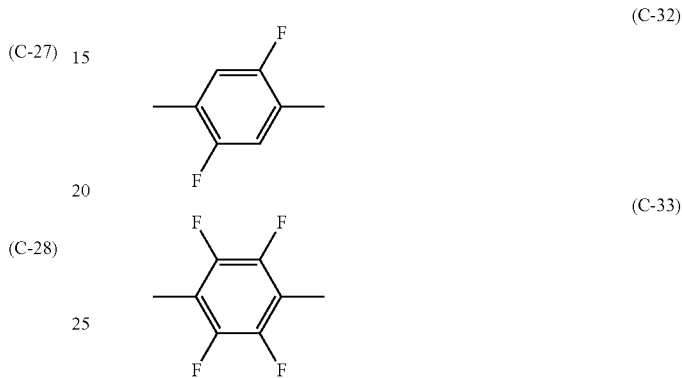

The halogen atom represented by X in the formula (V) includes a fluorine atom, a chlorine atom, a bromine atom and an iodine atom. From the standpoint of easiness of synthesis of a polymer compound, a bromine atom and an iodine atom are preferable, a bromine atom is further preferable.

Specifically, the method of carrying out the Suzuki coupling reaction includes a method of reacting in the presence of a base using a palladium catalyst as a catalyst in any solvent.

The palladium catalyst used in the Suzuki coupling reaction includes, for example, a Pd (0) catalyst and a Pd (II) catalyst, specifically, palladium[tetrakis(triphenylphosphine)], dichlorobis(triphenylphosphine)palladium, palladium acetate, tris(dibenzylideneacetone)dipalladium and bis(dibenzylideneacetone)palladium. Preferable from the standpoint of easiness of the reaction (polymerization) operation and the reaction (polymerization) speed are dichlorobis(triphenylphosphine)palladium, palladium acetate and tris(dibenzylideneacetone)dipalladium.

The addition amount of the palladium catalyst is not particularly restricted and may advantageously be an effective amount as a catalyst, and it is usually 0.0001 mol to 0.5 mol, preferably 0.0003 mol to 0.1 mol with respect to 1 mol of a compound represented by the formula (I).

In the case of use of palladium acetate as the palladium catalyst to be used in the Suzuki coupling reaction, a phosphorus compound such as triphenylphosphine, tri(o-tolyl)phosphine, tri(o-methoxyphenyl)phosphine and the like can be added as a ligand. In this case, the addition amount of the ligand is usually 0.5 mol to 100 mol, preferably 0.9 mol to 20 mol, further preferably 1 mol to 10 mol with respect to 1 mol of the palladium catalyst.

The base to be used in the Suzuki coupling reaction includes inorganic bases, organic bases, inorganic salts and the like. The inorganic base includes, for example, potassium carbonate, sodium carbonate, barium hydroxide and potassium phosphate. The organic base includes, for example, trimethylamine and tributylamine. The inorganic salt includes, for example, cesium fluoride.

The addition amount of the base is usually 0.5 mol to 100 mol, preferably 0.9 mol to 20 mol, further preferably 1 mol to 10 mol with respect to 1 mol of a compound represented by the formula (I).

The Suzuki coupling reaction is carried out usually in a solvent. From the standpoint of solubility of the polymer compound of the present invention, it is preferable to select at least one solvent from among tetrahydrofuran, toluene, xylene, chlorobenzene, 1-chloronaphthalene and 1-methylnaphthalene, it is further preferable to contain tetrahydrofuran, it is particularly preferable that the volume fraction of tetrahydrofuran occupying the total solvent volume fraction is 5% or more.

In the Suzuki coupling reaction, it is permissible that an aqueous solution containing a base is added to the reaction solution and the reaction is carried out in a two-phase system composed of an aqueous phase and an organic phase. In the case of use of an inorganic salt as a base, it is usual that an aqueous solution containing a base is added to the reaction solution and the reaction is performed, from the standpoint of solubility of the inorganic salt. In the case of use of the reactive compound represented by the formula (I) of the present invention, an aqueous solution containing potassium phosphate is preferable from the standpoint of reactivity.

In the case of reacting in a two-phase system, a phase transfer catalyst such as a quaternary ammonium salt and the like may be added if necessary.

The temperature for conducting the Suzuki coupling reaction is usually about 20 to 160° C. depending on a solvent. From the standpoint of thermal stability of a substrate and the reaction speed of a substrate, temperatures from 20 to 100° C. are preferable, temperatures from 20 to 80° C. are more preferable, and it is further preferable that the reaction is started at a low temperature of 20° C. to 40° C. and the temperature is raised up to 50° C. to 80° C. in a stepwise fashion. Further, it may also be permissible that the temperature is raised up to near the boiling point of a solvent and reflux is caused. Though time when the intended degree of polymerization is reached may be regarded as the end point, the reaction time is usually 0.1 hour to 100 hours. Times from 0.1 hour to 30 hours are preferable because of good efficiency.

The Suzuki coupling reaction is conducted in a reaction system not deactivating a palladium catalyst under an inert atmosphere such as an argon gas, a nitrogen gas and the like. For example, the reaction is conducted in a system deaerated sufficiently with an argon gas, a nitrogen gas or the like. Specifically, an atmosphere in a polymerization vessel (reaction system) is purged sufficiently and deaerated with a nitrogen gas, then, a compound represented by the formula (I), a compound represented by the formula (V) and a palladium catalyst, for example, tris(dibenzylideneacetone) dipalladium (0) or [tri(tertiary butyl)phosphonium]tetrafluoroborate are charged in this polymerization vessel, and further, an atmosphere in the polymerization vessel is purged sufficiently and deaerated with a nitrogen gas, then, a solvent deaerated by previously bubbling with a nitrogen gas, for example, tetrahydrofuran, is added, then, a base deaerated by previously bubbling with a nitrogen gas, for example, a potassium phosphate aqueous solution is dropped into this solution, then, the mixture is heated to raise its temperature, and for example, polymerization is performed while keeping an inert atmosphere for 3 hours at the reflux temperature.

In the case of conducting the Suzuki coupling reaction using the reactive compound represented by the formula (I) of the present invention, it is preferable that a compound represented by the formula (V), a palladium catalyst, a base and a reaction solvent are charged, then, the reactive compound represented by the formula (I) is dropped over a time of 0.1 minute to 100 minutes and it is preferable that the reaction is started when the reaction temperature in the system is 20° C. to 50° C. and the temperature is raised up to 50° C. to 100° C. in a stepwise fashion over a period of 1 minute to 100 minutes, from the standpoint of reactivity.

The polystyrene-equivalent number average molecular weight of the polymer compound is preferably $1 \times 10^3$ to $1 \times 10^8$. When the polystyrene-equivalent number average molecular weight is $1 \times 10^3$ or more, a tough film is obtained easily. In contrast, when $1 \times 10^8$ or less, solubility is high and fabrication of a film is easy.

The end group of the polymer compound of the present invention may be protected with a stable group since if a polymerization active group remains intact, there is a possibility of lowering of the life and properties of a device obtained when the compound is used for fabrication of the device. Those having a conjugate bond continuous with the conjugated structure of the main chain are preferable, and further, for example, structures having a linkage to an aryl group or a heterocyclic group via a vinylene group may also be permissible.

The compound represented by the following formula (B):

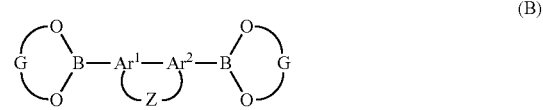

(Here, $Ar^1$, $Ar^2$, G and Z each represent the same meaning as described above.)

as one embodiment of the reactive compound of the present invention can be produced, for example, by subjecting a compound represented by the following formula (C):

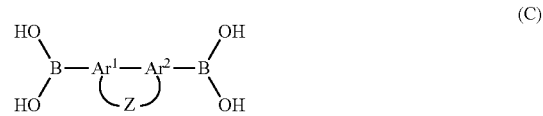

(Here, $Ar^1$, $Ar^2$ and Z each represent the same meaning as described above.)

and a compound represented by the following formula (D):

(Here, G represents the same meaning as described above.) to a dehydration reaction.

The use amount of the compound represented by the formula (D) is usually 2 to 10 mol, preferably 2 to 4 mol with respect to 1 mol of the compound represented by the formula (C).

The dehydration reaction is conducted usually in a solvent. The solvent includes toluene, xylene, mesitylene and the like, and toluene is preferable.

The dehydration reaction can be conducted in the presence of an acid. As the acid, organic acids such as p-toluenesulfonic acid and the like and inorganic acids such as concentrated sulfuric acid, dilute sulfuric acid and the like can be used. In the case of use of an acid, the addition amount of the acid is not particularly restricted, and it is usually 0.001 mol to 100 mol, preferably 0.01 mol to 10 mol with respect to 1 mol of the compound represented by the formula (C).

For example, the dehydration reaction can be conducted while discharging water generated by the reaction out of the reaction system. The method of discharging water out of the reaction system includes, for example, a method using a Dean-Stark tube.

The temperature of the dehydration reaction is usually 40 to 200° C., preferably 60 to 120° C. The time of the dehydration reaction is usually 1 minute to 50 hours, preferably 10 minutes to 10 hours.

The resultant compound (B) can be purified easily by a recrystallization method.

The compound represented by the formula (C) can be produced, for example, by reacting a compound represented by the following formula (E):

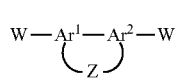
(E)

(Here, $Ar^1$, $Ar^2$ and Z each represent the same meaning as described above, a plurality of W are the same or different from each other, and represent a hydrogen atom, a bromine atom or an iodine atom.)
with a metalating agent, to produce a compound represented by the formula (F):

(F)

(Here, $Ar^1$, $Ar^2$ and Z each represent the same meaning as described above, a plurality of M are the same or different from each other, and represent a metal atom.) and reacting the compound represented by the formula (F) with a dihydroxyboronating agent.

The compound represented by the formula (E) in which W is a hydrogen atom can be produced by using a known method. The compound represented by the formula (E) in which W is a halogen atom selected from a bromine atom and an iodine atom can be produced by using a known method. For example, the compound represented by the formula (E) in which W is a hydrogen atom can be produced by treating with a halogenating agent such as N-bromosuccinimide and the like according to a known method.

It is preferable that W is a hydrogen atom in the formula (E) since production of the compound is easy.

The reaction of the compound represented by the formula (E) with a metalation agent is conducted usually in a solvent. As the solvent, ether solvents such as diethyl ether, tetrahydrofuran and the like are preferable.

As the metalation agent, alkyllithium and lithium amide are preferable. Specific examples of the alkyllithium include -butyllithium, sec-butyllithium and ter-butyllithium. Specific examples the lithium amide include lithiumdiisopropyl amide.

The use amount of the metalation agent is usually 2 to 10 mol, preferably 2 to 4 mol with respect to 1 mol of the compound represented by the formula (E).

The reaction temperature is usually −78° C. to 50° C., preferably −78° C. to 20° C. The reaction time is usually 5 minutes to 5 hours, preferably 10 minutes to 3 hours.

In the compound represented by the formula (F), M is preferably a lithium atom.

As the dihydroxyboronating agent, trialkyloxyborane is preferable, and specific examples thereof include trimethoxyborane, triisopropoxyborane and the like.

The use amount of the dihydroxyboronating agent is usually 2 to 10 mol, preferably 2 to 4 mol with respect to 1 mol of the compound represented by the formula (F).

The temperature of the dihydroxyboronating reaction is usually −78° C. to 80° C., preferably −20° C. to 80° C. The reaction time is usually 5 minutes to 5 hours, preferably 10 minutes to 3 hours.

One embodiment of the method of producing a compound represented by the formula (B) is a production method in which a compound represented by the formula (E) and a metalation agent are reacted to produce a compound represented by the formula (F), the compound represented by the formula (F) and a dihydroxyboronating agent are reacted to produce a compound represented by the formula (C), and the compound represented by the formula (C) and a compound represented by the formula (D) are subjected to a dehydration reaction.

The formulae (Ar'-1) to (Ar'-5) as the reactive compound of the present invention can be synthesized, for example, by using compounds represented by the formulae (Ar-1) to (Ar-10) as raw materials.

(Ar-1)

(Ar-2)

(Ar-3)

(Ar-4)

(Ar-5)

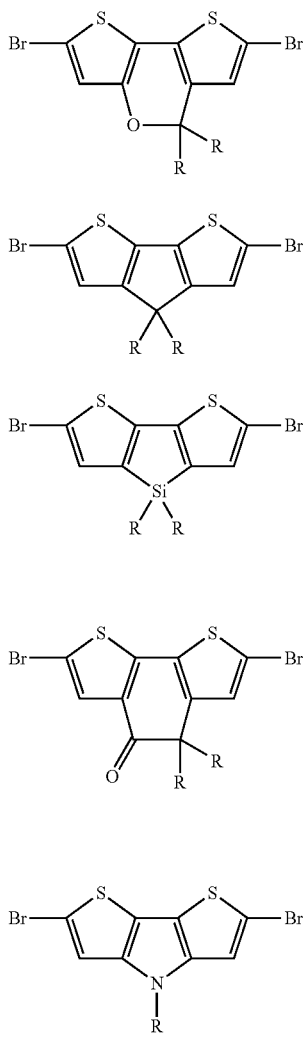

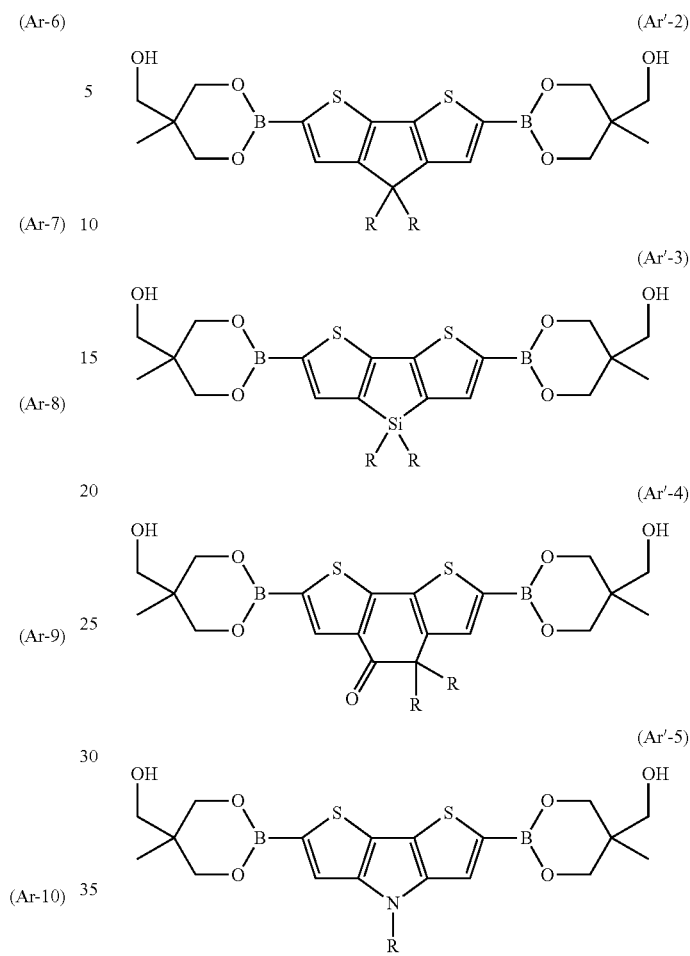

[In the formulae, R represents the same meaning as described above.]

In synthesizing the reactive compound of the present invention, the formula (Ar-1), the formula (Ar-2), the formula (Ar-3), the formula (Ar-4), the formula (Ar-6), the formula (Ar-7), the formula (Ar-8) and the formula (Ar-9) are preferable, the formula (Ar-1), the formula (Ar-2) and the formula (Ar-3) are more preferable, the formula (Ar-1) and the formula (Ar-3) are further preferable, the formula (Ar-1) is particularly preferable, from the standpoint of easiness of synthesis.

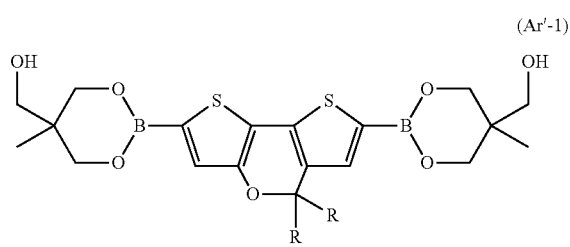

[In the formulae, R represents the same meaning as described above.]

The compound represented by the formulae (Ar-1) to (Ar-10) can be converted into the reactive compound represented by the formula (I) as described below: for example, the compound represented by the formulae (Ar-1) to (Ar-10) is dilithiated using a base such as -butyllithium and the like in a diethyl ether solvent, then, trimethoxyborane, triisopropoxyborane or the like is allowed to act on this to synthesize the corresponding boronic acid, then, the acid is esterified with a polyhydric alcohol such as 2-hydroxymethylene-2-methyl-1,3-propanediol and the like.

The purity of the reactive compound in the present invention can be easily enhanced by a recrystallization method. The solvent used for recrystallization includes n-pentane, n-hexane, n-heptane, n-octane, n-nonane, n-decane, cyclohexane, benzene, toluene, o-xylene, m-xylene, p-xylene, mesitylene and the like, and may be a single solvent or a mixed solvent. A mixed solvent composed of cyclohexane and toluene is preferably mentioned.

Reactive compounds represented by the following formulae (Ar''-1) to (Ar''-5) can be synthesized by using compounds represented by the formulae (Ar'-1) to (Ar'-5) as raw materials, corresponding to the reactive compound of the present invention.

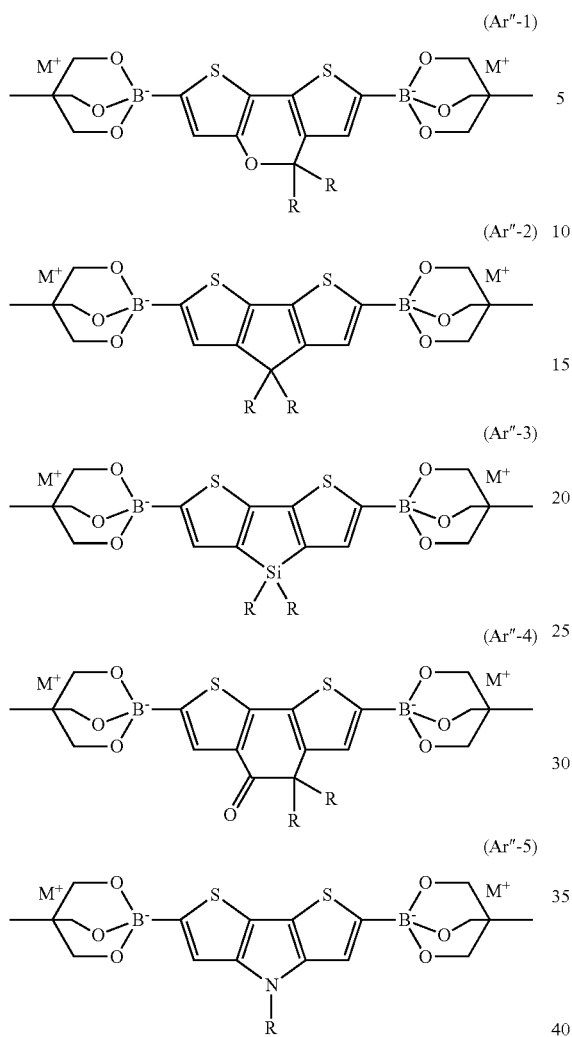

(Ar″-1)
(Ar″-2)
(Ar″-3)
(Ar″-4)
(Ar″-5)

[In the formulae, R represents the same meaning as described above. In the formulae, M represents a lithium atom, a sodium atom or a potassium atom.]

The polymer compound of the present invention can be produced also when the reactive compounds represented by the formulae (Ar″-1) to (Ar″-5) are used, in addition to the reactive compound represented by the formula (I).

Since the polymer compound of the present invention can exert high electron and/or hole transportability, when an organic film containing the polymer compound is used in a device, electrons and holes injected from electrodes or charges generated by optical absorption can be transported. Utilizing these properties, the compound can be suitably used in various electronic devices such as photoelectric conversion devices, organic film transistors, organic electroluminescent devices and the like.

For example, in a photoelectric conversion device, the polymer compound of the present invention is used as a material of an active layer. Further, in an organic film transistor, the polymer compound of the present invention is used in an organic semiconductor layer (active layer) acting as a current pathway between a source electrode and a drain electrode. Furthermore, in an organic electroluminescent device, the polymer compound of the present invention is used in a light emitting layer.

EXAMPLES

Examples will be shown below for illustrating the present invention further in detail, but the present invention is not limited to them.

(NMR (Nuclear Magnetic Resonance) Measurement)

A compound was dissolved in deuterated chloroform, and NMR was measured using an NMR apparatus (manufactured by Varian, INOVA300).

(LC (Liquid Chromatography) Measurement)

A compound was dissolved in tetrahydrofuran, and LC measurement was performed using a LC apparatus (manufactured by Shimadzu Corporation, LC-20A).

Example 1

Synthesis of Compound 3

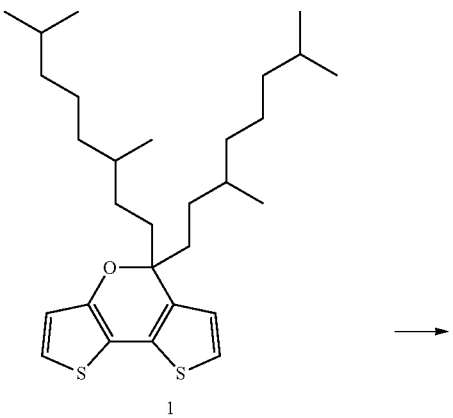

1

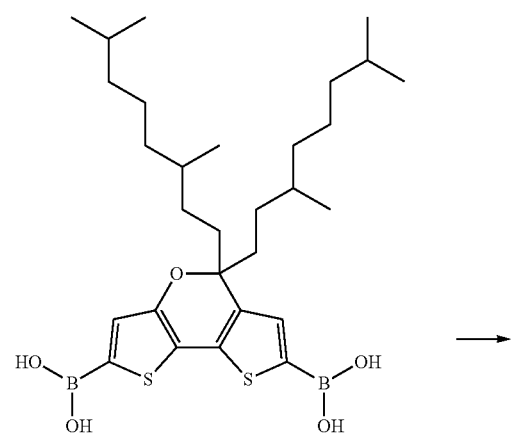

2

53
-continued

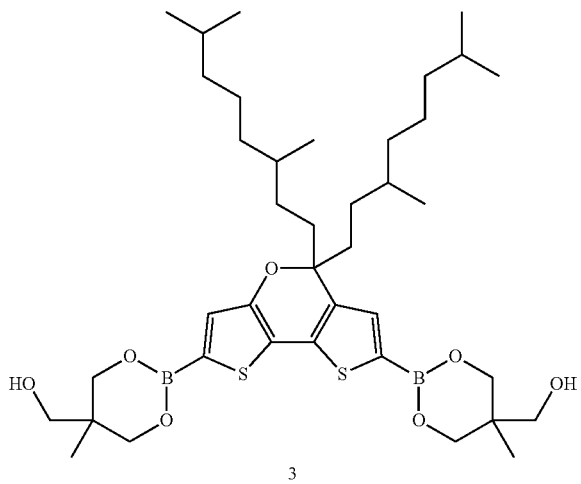

3

Into a four-necked flask were added 9.50 g (20.00 mmol) of a compound 1 synthesized by a method described in International Publication (WO2011/052709A1) and 100 mL of diethyl ether, and an argon gas was introduced into and bubbled through the resultant reaction liquid at room temperature (25° C.) for 30 minutes. The reaction liquid was cooled down to −70° C., then, 29.3 mL of a -butyllithium solution (1.64 mol/L, hexane solution) was added, and the mixture was stirred at room temperature for 2 hours. The reaction liquid was cooled down to −70° C., then, 5.20 g (50.00 mmol) of trimethoxyborane was added, and the mixture was stirred for 2 hours at −70° C. with no variation of temperature. Disappearance of a peak of the compound 1 and generation of a compound 2 were confirmed by liquid chromatography, and the reaction was terminated.

Into the reaction liquid was charged a 10 w % acetic acid aqueous solution (100 mL), and a liquid separating operation was conducted using ethyl acetate (100 mL), and an organic layer was extracted. To the organic layer were added toluene (100 mL) and 4.81 g (40.00 mmol) of 2-hydroxymethylene-2-methyl-1,3-propanediol, and a dehydration operation using a Dean-Stark tube was conducted for 30 minutes. Disappearance of a peak of the compound 2 and generation of a compound 3 were confirmed by liquid chromatography, and the reaction was terminated.

After removal of the organic solvent, a green-brown coarse crystal was obtained. A recrystallization operation using cyclohexane/toluene was performed, to obtain 7.9 g of a pale yellow compound 3. The LC purity was 99.5%.

$^1$H-NMR (CDCl$_3$, δ (ppm)): 0.798 (q, 6H), 0.840 (q, 12H), 0.979 (s, 3H), 0.991 (s, 3H), 1.05-1.54 (m, 20H), 1.840 (m, 4H), 3.633 (m, 4H), 3.805 (m, 4H), 4.015 (m, 4H), 7.051 (s, 1H), 7.111 (s, 1H)

54

Example 2

Synthesis of Compound 6

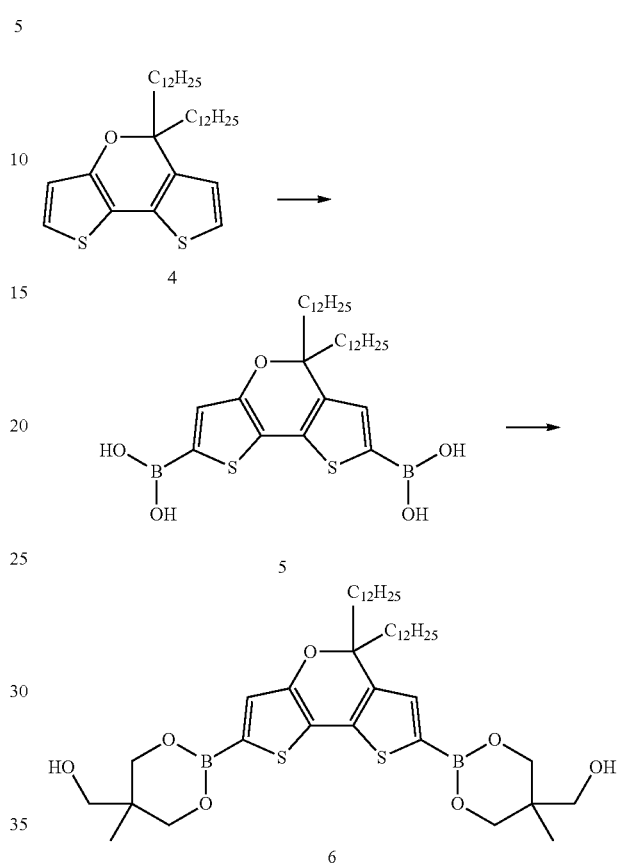

Into a four-necked flask were added 10.62 g (20.00 mmol) of a compound 4 synthesized by a method described in International Publication (WO2011/052709A1) and 100 mL of diethyl ether, and an argon gas was introduced into and bubbled through the resultant reaction liquid at room temperature (25° C.) for 30 minutes. The reaction liquid was cooled down to −70° C., then, 29.3 mL of a -butyllithium solution (1.64 mol/L, hexane solution) was added, and the mixture was stirred at room temperature for 2 hours. The reaction liquid was cooled down to −70° C., then, 5.20 g (50.00 mmol) of trimethoxyborane was added, and the mixture was stirred for 2 hours at −70° C. with no variation of temperature. Disappearance of a peak of the compound 4 and generation of a compound 5 were confirmed by liquid chromatography, and the reaction was terminated.

Into the reaction liquid was charged a 10 w % acetic acid aqueous solution (100 mL), and a liquid separating operation was conducted using ethyl acetate (100 mL), and an organic layer was extracted. To the organic layer were added toluene (100 mL) and 4.81 g (40.00 mmol) of 2-hydroxymethylene-2-methyl-1,3-propanediol, and a dehydration operation using a Dean-Stark tube was conducted for 30 minutes. Disappearance of a peak of the compound 5 and generation of a compound 6 were confirmed by liquid chromatography, and the reaction was terminated.

After removal of the organic solvent, a green-brown coarse crystal was obtained. A recrystallization operation using cyclohexane/toluene was performed, to obtain 5.5 g of a pale yellow compound 6. The LC purity was 99.8%.

¹H-NMR (CDCl₃, δ (ppm)): 0.875 (t, 6H), 0.986 (d, 6H), 1.16-1.28 (m, 36H), 1.494 (m, 4H), 1.830 (m, 4H), 3.635 (m, 4H), 3.804 (m, 4H), 3.998 (m, 4H), 7.047 (s, 1H), 7.113 (s, 1H)

Example 3

Synthesis of Compound 9

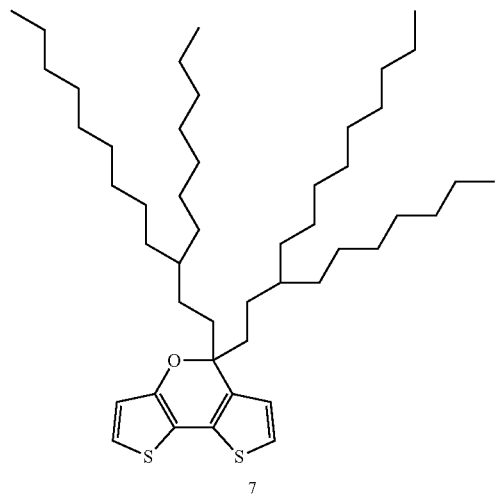

7

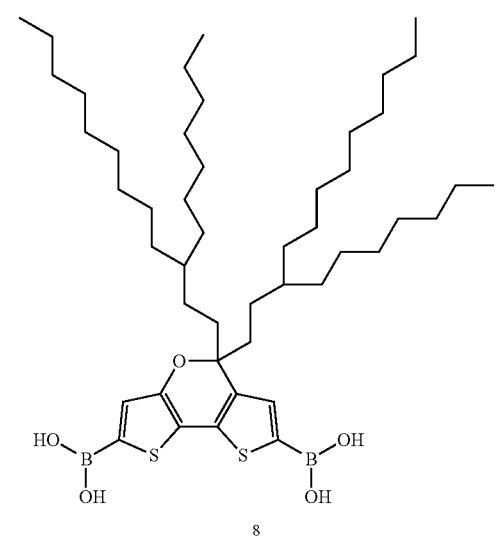

8

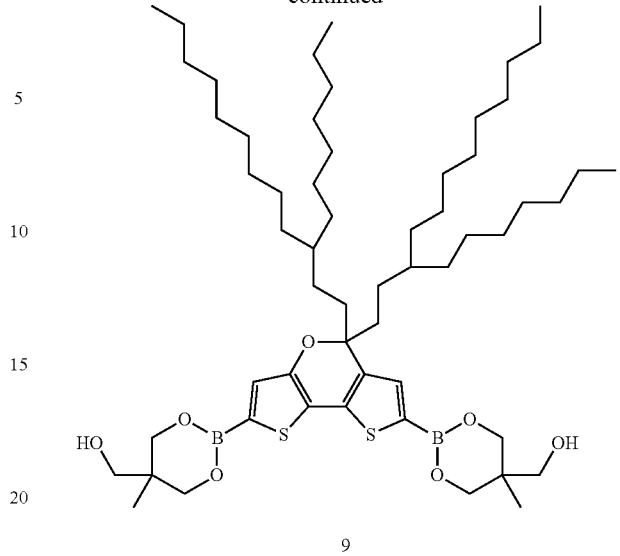

9

Into a four-necked flask were added 2.91 g (4.00 mmol) of a compound 7 synthesized by a method described in International Publication (WO2011/052709A1) and 20 mL of diethyl ether, an argon gas was introduced into and bubbled through the resultant reaction liquid at room temperature (25° C.) for 30 minutes. The reaction liquid was cooled down to −70° C., then, 5.9 mL of a -butyllithium solution (1.64 mol/L, hexane solution) was added, and the mixture was stirred at room temperature for 2 hours. The reaction liquid was cooled down to −70° C., then, 1.04 g (10.00 mmol) of trimethoxyborane was added, and the mixture was stirred for 2 hours at −70° C. with not variation of temperature. Disappearance of a peak of the compound 7 and generation of a compound 8 were confirmed by liquid chromatography, and the reaction was terminated.

Into the reaction liquid was charged a 10 w % acetic acid aqueous solution (20 mL), and a liquid separating operation was conducted using ethyl acetate (20 mL), and an organic layer was extracted. To the organic layer were added toluene (20 mL) and 961 mg (80.00 mmol) of 2-hydroxymethylene-2-methyl-1,3-propanediol, and a dehydration operation using a Dean-Stark tube was conducted for 30 minutes. Disappearance of a peak of the compound 8 and generation of a compound 9 were confirmed by liquid chromatography, and the reaction was terminated.

After removal of the organic solvent, a green-brown coarse crystal was obtained. A recrystallization operation using cyclohexane/toluene was performed, to obtain 1.2 g of a pale yellow compound 9. The LC purity was 99.6%.

¹H-NMR (CDCl₃, δ (ppm)): 0.882 (t, 12H), 0.984 (d, 6H), 1.00-1.40 (m, 58H), 1.490 (m, 4H), 1.801 (m, 4H), 3.647 (m, 4H), 3.788 (m, 4H), 3.983 (m, 4H), 7.051 (s, 1H), 7.122 (s, 1H)

Synthesis Example 1

Synthesis of Compound 22

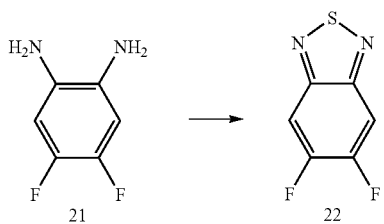 [SMILES: Nc1cc(F)c(F)cc1N ; Fc1cc2nsnc2cc1F]

Into a 500 ml flask were charged 10.2 g (70.8 mmol) of 4,5-difluoro-1,2-diaminobenzene (compound 21) (manufactured by Tokyo Chemical Industry Co., Ltd.) and 150 mL of pyridine and a uniform solution was obtained. The flask was cooled down to 0° C., and 16.0 g (134 mmol) of thionyl chloride was dropped into the flask. After dropping, the flask was warmed at 25° C., and the solution was reacted for 6 hours. Thereafter, 250 ml of water was added to the reaction liquid, and further, chloroform was added and an organic layer containing the reaction product was extracted. The organic layer as a chloroform solution was dried over sodium sulfate, and filtrated. The filtrate was concentrated by an evaporator, and the deposited solid was purified by recrystallization. As the solvent for recrystallization, methanol was used. After purification, 10.5 g (61.0 mmol) of a compound 22 was obtained.

$^1$H-NMR (CDCl$_3$, δ (ppm)): 7.75 (s, 2H)
$^{19}$F-NMR (CDCl$_3$, δ (ppm)): −128.3 (s, 2F)

Synthesis Example 14

Synthesis of Compound 23

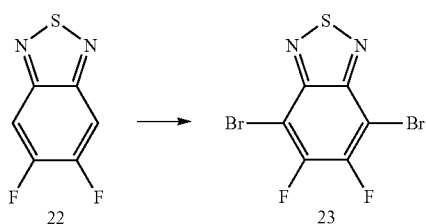 [SMILES: Fc1cc2nsnc2cc1F ; Fc1c(F)c(Br)c2nsnc2c1Br]

Into a 100 mL flask were charged 2.00 g (11.6 mmol) of the compound 22 and 0.20 g (3.58 mmol) of an iron powder, and the flask was heated at 90° C. Into this flask, 31 g (194 mmol) of bromine was dropped over a period of 1 hour. After dropping, the reaction liquid was stirred at 90° C. for 38 hours. Thereafter, the flask was cooled down to room temperature (25° C.), and 100 mL of chloroform was added for dilution. The resultant solution was poured into 300 mL of a 5 wt % sodium sulfite aqueous solution, and the mixture was stirred for 1 hour. An organic layer of the resultant mixed liquid was separated by a separating funnel, and an aqueous layer was extracted with chloroform three times. The resultant extraction liquid was mixed with the organic layer, and the mixed solution was dried over sodium sulfate. After filtration, the filtrate was concentrated by an evaporator and the solvent was distilled off. The resultant yellow solid was dissolved in 90 mL of methanol heated at 55° C., then, the solution was cooled down to 25° C. The deposited crystal was recovered by filtration, then, dried under reduced pressure at room temperature (25° C.), to obtain 1.50 g of a compound 23.

$^{19}$F-NMR (CDCl$_3$, δ (ppm)): −118.9 (s, 2F)

Example 4

Synthesis of Polymer A

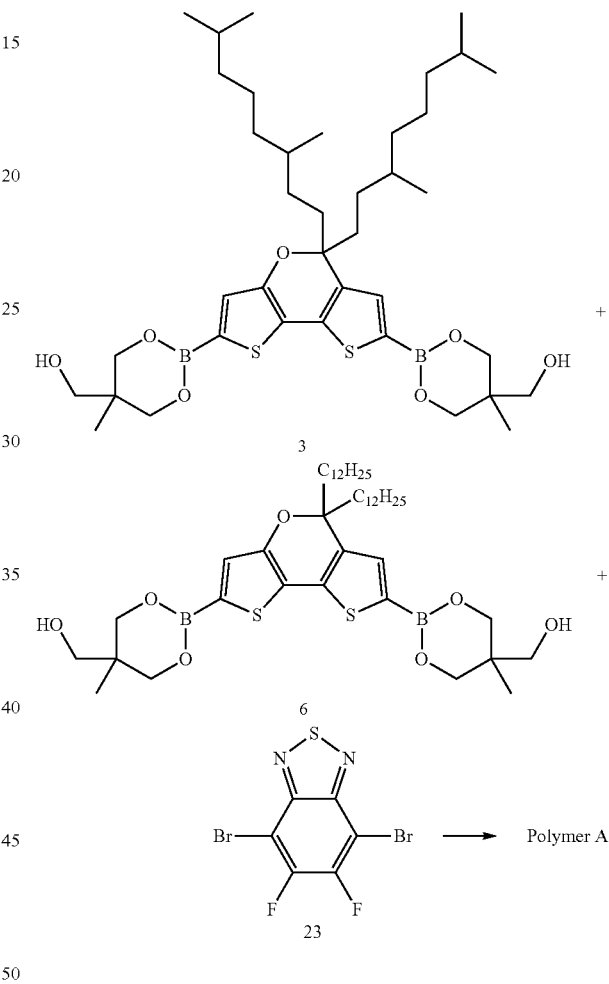

Into a four-necked flask were added 197.9 mg (0.600 mmol) of the compound 23 and 15 mL of tetrahydrofuran, and an argon gas was introduced into and bubbled through the resultant reaction liquid at room temperature (25° C.) for 30 minutes. Thereafter, to the reaction liquid were added 27.47 mg (0.03 mmol) of tris(dibenzylideneacetone)dipalladium, 34.82 mg (0.12 mmol) of [tri(tertiary butyl)phosphonium]tetrafluoroborate and 2.0 mL (6.0 mmol) of a 3 mol/L potassium phosphate aqueous solution. While stirring at a temperature within system of 25° C., a solution obtained by dissolving 219.2 mg (0.300 mmol) of the compound 3 and 236.0 mg (0.300 mmol) of the compound 6 in 15 mL of 1-chloronaphthalene was dropped over a period of 10 minutes. Thereafter, the temperature of an oil bath was raised up to 80° C. over a period of 10 minutes and the reaction continued, and stirring of the solution was continued for 2 hours in total. At this moment, the temperature within the system was 60° C. Thereafter, to the reaction liquid was added 60.0 mg (0.492 mmol) of phenylboric acid, and the mixture was stirred further for 1 hour, then, the reaction was terminated. The reaction was conducted under an argon atmosphere. Thereafter, an organic layer was washed with 30 mL of a 10 wt % acetic acid aqueous solution three times, further with 30 mL of water once, and poured into acetone to cause deposition of a polymer which was then filtrated and dried, to obtain a coarsely purified polymer.

The coarsely purified polymer was dissolved in orthodichlorobenzene. The orthodichlorobenzene solution was allowed to pass through an alumina/silica gel column, and the resultant solution was poured into methanol to cause deposition of a polymer. The polymer was filtrated, then, dried, to obtain 256 mg of a polymer A.

Example 5

Synthesis of Polymer B

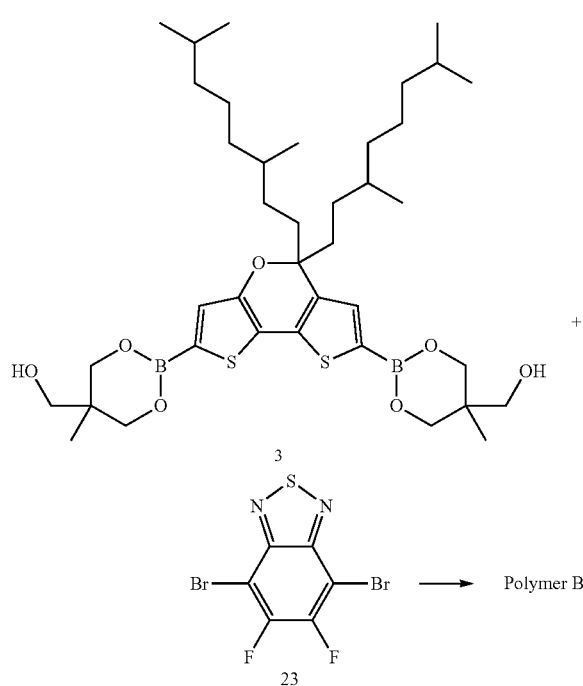

Into a four-necked flask were added 99.0 mg (0.300 mmol) of the compound 23 and 7.5 mL of tetrahydrofuran, and an argon gas was introduced into and bubbled through the resultant reaction liquid at room temperature (25° C.) for 30 minutes. Thereafter, to the reaction liquid were added 13.74 mg (0.015 mmol) of tris(dibenzylideneacetone)dipalladium, 17.41 mg (0.06 mmol) of [tri(tertiary butyl)phosphonium]tetrafluoroborate and 1.0 mL (3.0 mmol) of a 3 mol/L potassium phosphate aqueous solution. While stirring at a temperature within the system of 25° C., a solution obtained by dissolving 219.2 mg (0.300 mmol) of the compound 3 in 7.5 mL of chlorobenzene was dropped over a period of 10 minutes. Thereafter, the temperature of an oil bath was raised up to 80° C. over a period of 10 minutes and the reaction was continued, and stirring of the solution was continued for 2 hours in total. At this moment, the temperature within the system was 60° C. Thereafter, 30.0 mg (0.246 mmol) of phenylboric acid was added to the reaction liquid, and the mixture was further stirred for 1 hour, then, the reaction was terminated. The reaction was conducted under an argon atmosphere. Thereafter, an organic layer was washed with 15 mL of a 10 wt % acetic acid aqueous solution three times, further with 15 mL of water once, and poured into acetone to cause deposition of a polymer which was then filtrated and dried, to obtain a coarsely purified polymer.

The coarsely purified polymer was dissolved in orthodichlorobenzene. The orthodichlorobenzene solution was allowed to pass through an alumina/silica gel column, and the resultant solution was poured into methanol to cause deposition of a polymer. The polymer was filtrated, then, dried, to obtain 77 mg of a polymer B.

Example 6

Synthesis of Polymer C

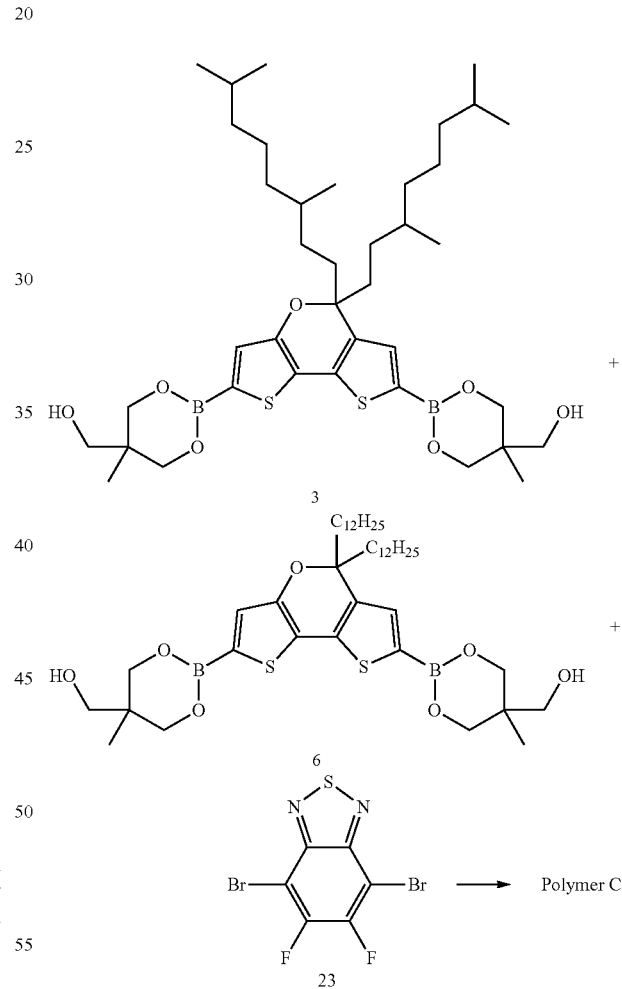

Into a four-necked flask were added 197.9 mg (0.600 mmol) of the compound 23 and 15 mL of tetrahydrofuran, and an argon gas was introduced into and bubbled through the resultant reaction liquid at room temperature (25° C.) for 30 minutes. Thereafter, to the reaction liquid were added 27.47 mg (0.03 mmol) of tris(dibenzylideneacetone)dipalladium, 34.82 mg (0.12 mmol) of [tri(tertiary butyl)phosphonium]tetrafluoroborate and 2.0 mL (6.0 mmol) of a 3 mol/L potassium phosphate aqueous solution. While stirring at a temperature within the system of 25° C., a solution obtained by dissolving 219.2 mg (0.300 mmol) of the compound 3 and 236.0 mg (0.300 mmol) of the compound 6 in 15 mL of tetrahydrofuran was dropped over a period of 10 minutes. Thereafter, the temperature of an oil bath was raised up to 80° C. over a period of 10 minutes and the reaction was continued, and stirring of the solution was continued for 2 hours in total. At this moment, the temperature within the system was 60° C. Thereafter, 60.0 mg (0.492 mmol) of phenylboric acid was added to the reaction liquid, and the mixture was further stirred for 1 hour, then, the reaction was terminated. The reaction was conducted under an argon atmosphere. Thereafter, an organic layer was washed with 30 mL of a 10 wt % acetic acid aqueous solution three times, further with 30 mL of water once, and poured into acetone to cause deposition of a polymer which was then filtrated and dried, to obtain a coarsely purified polymer.

The coarsely purified polymer was dissolved in orthodichlorobenzene. The orthodichlorobenzene solution was allowed to pass through an alumina/silica gel column, and the resultant solution was poured into methanol to cause deposition of a polymer. The polymer was filtrated, then, dried, to obtain 316 mg of a polymer C.

Example 6

Synthesis of Polymer D

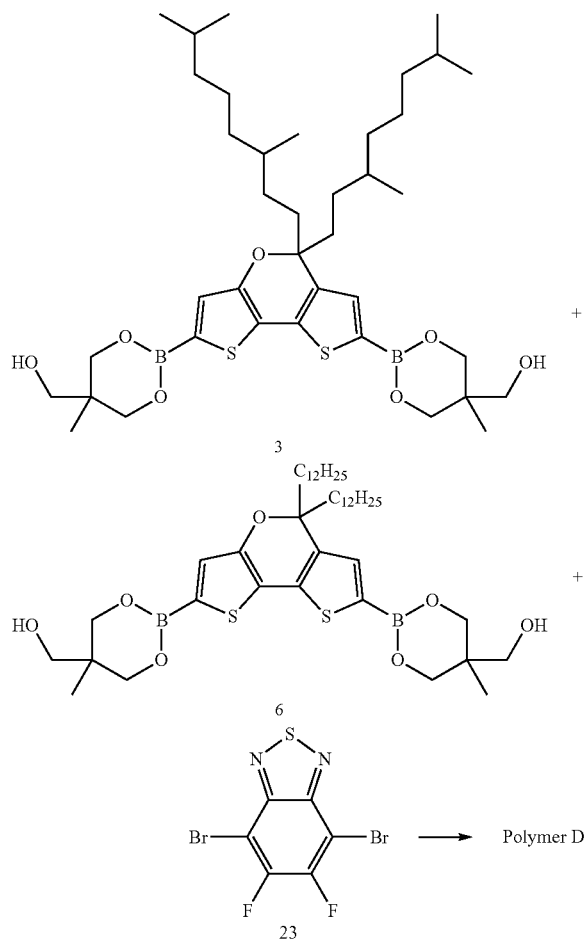

Into a four-necked flask were added 197.9 mg (0.600 mmol) of the compound 23 and 21 mL of tetrahydrofuran, and an argon gas was introduced into and bubbled through the resultant reaction liquid at room temperature (25° C.) for 30 minutes. Thereafter, to the reaction liquid were added 27.47 mg (0.03 mmol) of tris(dibenzylideneacetone)dipalladium, 34.82 mg (0.12 mmol) of [tri(tertiary butyl)phosphonium]tetrafluoroborate and 2.0 mL (6.0 mmol) of a 3 mol/L potassium phosphate aqueous solution. While stirring at a temperature within the system of 25° C., a solution obtained by dissolving 219.2 mg (0.300 mmol) of the compound 3 and 236.0 mg (0.300 mmol) of the compound 6 in 9 mL of toluene was dropped over a period of 10 minutes. Thereafter, the temperature of an oil bath was raised up to 80° C. over a period of 10 minutes and the reaction was continued, and stirring of the solution was continued for 2 hours in total. At this moment, the temperature within the system was 60° C. Thereafter, 60.0 mg (0.492 mmol) of phenylboric acid was added to the reaction liquid, and the mixture was further stirred for 1 hour, then, the reaction was terminated. The reaction was conducted under an argon atmosphere. Thereafter, an organic layer was washed with 30 mL of a 10 wt % acetic acid aqueous solution three times, further with 30 mL of water once, and poured into acetone to cause deposition of a polymer which was then filtrated and dried, to obtain a coarsely purified polymer.

The coarsely purified polymer was dissolved in orthodichlorobenzene. The orthodichlorobenzene solution was allowed to pass through an alumina/silica gel column, and the resultant solution was poured into methanol to cause deposition of a polymer. The polymer was filtrated, then, dried, to obtain 200 mg of a polymer D.

The solvents used for production of the polymers A to D are shown in Table 1 below.

TABLE 1

|  | polymerization solvent 1 | polymerization solvent 2 |
|---|---|---|
| polymer A | tetrahydrofuran | 1-chloronaphthalene |
| polymer B | tetrahydrofuran | chlorobenzene |
| polymer C | tetrahydrofuran |  |
| polymer D | tetrahydrofuran | toluene |

INDUSTRIAL APPLICABILITY

Since an improvement in the purity of the reactive compound of the present invention is easy, the present invention is extremely useful.

The invention claimed is:
1. A reactive compound represented by the following formula (I):

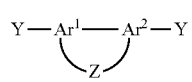

in the formula (I), Z represents a divalent group, a plurality of Y may be the same or different, and represent a monovalent boronate residue having at least one hydroxyl group, $Ar^1$ and $Ar^2$ may be the same or different, and represent a trivalent heterocyclic group.

2. The reactive compound according to claim 1, wherein Y is a group represented by the following formula (Y'-1), (Y'-2) or (Y'-3):

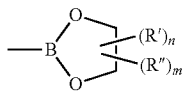
(Y'-1)

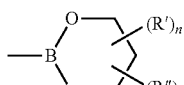
(Y'-2)

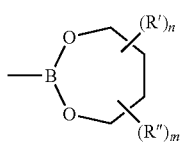
(Y'-3)

in the formulae (Y'-1), (Y'-2) and (Y'-3), R' is a substituent represented by the following formula (R'-1), (R'-2) or (R'-3), R" represents a hydrogen atom, a methyl group or an ethyl group, n and m each represent an integer, and satisfy n≥1, m≥0 and n+m≤4,

(R'-1)

(R'-2)

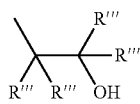
(R'-3)

in the formulae (R'-1), (R'-2) and (R'-3), a plurality of R''' are the same or different from each other, and represent a hydrogen atom, a methyl group or an ethyl group.

3. The reactive compound according to claim 1, wherein Z is a group represented by any one of the following formulae (Z-1) to (Z-7):

(Z-1)

(Z-2)

(Z-3)

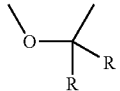
(Z-4)

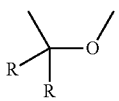
(Z-5)

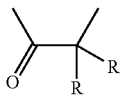
(Z-6)

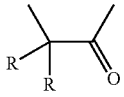
(Z-7)

in the formulae (Z-1) to (Z-7), a plurality of R are the same or different from each other, and represent a hydrogen atom, a halogen atom or a substituent.

4. The reactive compound according to claim 1, wherein the reactive compound represented by the formula (I) is a compound represented by the following formula (II):

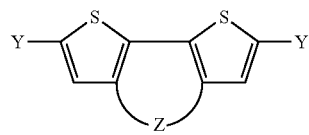
(II)

in the formula (II), Z represents the same meaning as described above, Y represents the same meaning as described above.

5. The reactive compound according to claim 1, wherein Y is a group represented by the following formula (Y-1), (Y-2) or (Y-3):

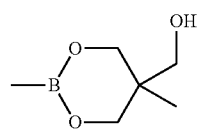
(Y-1)

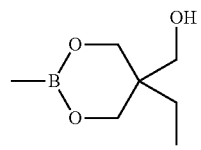
(Y-2)

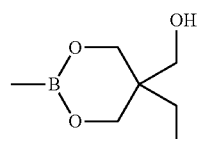
(Y-3)

6. The reactive compound according to claim 1, wherein the reactive compound represented by the formula (I) is a compound represented by the following formula (III-1) or (III-2):

(III-1)

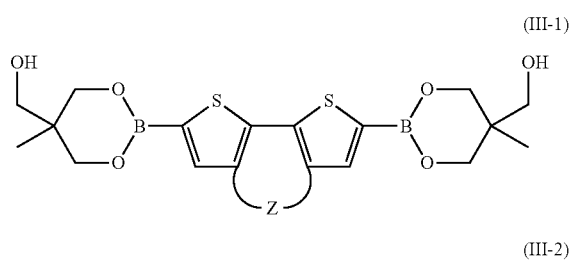

(III-2)

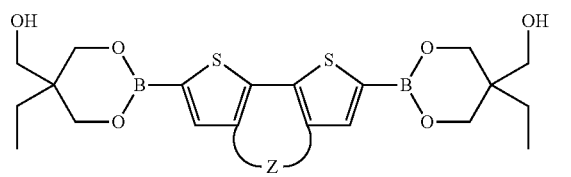

in the formulae (III-1) and (III-2), Z represents the same meaning as described above.

7. The reactive compound according to claim 1, wherein the reactive compound represented by the formula (I) is a compound represented by the following formula (IV-1) or (IV-2):

(IV-1)

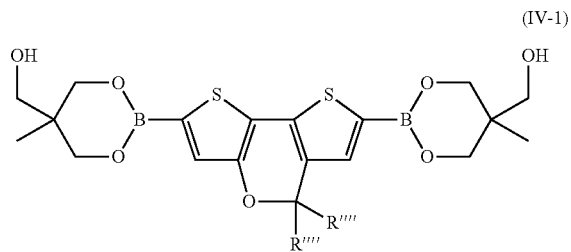

(IV-2)

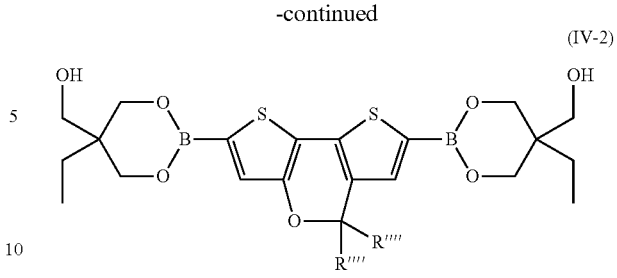

in the formulae (IV-1) and (IV-2), a plurality of R"" are the same or different from each other, and represent a hydrogen atom or a substituent.

8. A method of producing a polymer compound containing a constituent unit represented by the following formula (VI) and a constituent unit represented by the following formula (VII), (VI)

(VII)

ing reacting the reactive compound according to claim 1 with a compound represented by the following formula (V):

$$X—Ar^3—X \quad (V)$$

in the formula (VI), $Ar^1$, $Ar^2$ and Z represent the same meaning as described above, in the formula (VII), $Ar^3$ represents a divalent aromatic hydrocarbon group or a divalent heterocyclic group, in the formula (V), $Ar^3$ represents the same meaning as described above, and a plurality of X are the same or different from each other, and represent a halogen atom.

\* \* \* \* \*